US010292850B2

(12) United States Patent
Vad et al.

(10) Patent No.: US 10,292,850 B2
(45) Date of Patent: May 21, 2019

(54) DEPLOYMENT HANDLE FOR A PROSTHESIS DELIVERY DEVICE

(71) Applicant: Cook Medical Technologies LLC, Bloomington, IN (US)

(72) Inventors: Siddharth Vad, Bloomington, IN (US); Edwin Macatangay, Bloomington, IN (US); Wen Hong Neoh, Bloomington, IN (US); Eugene Skelton, Dublin (IE); Anthony Wright, Dublin (IE)

(73) Assignee: Cook Medical Technologies LLC, Bloomington, IN (US)

( * ) Notice: Subject to any disclaimer, the term of this patent is extended or adjusted under 35 U.S.C. 154(b) by 279 days.

(21) Appl. No.: 14/931,311

(22) Filed: Nov. 3, 2015

(65) Prior Publication Data

US 2016/0135972 A1    May 19, 2016

Related U.S. Application Data

(60) Provisional application No. 62/074,766, filed on Nov. 4, 2014.

(51) Int. Cl.
*A61F 2/966* (2013.01)
*A61F 2/07* (2013.01)
(Continued)

(52) U.S. Cl.
CPC ............... *A61F 2/966* (2013.01); *A61F 2/07* (2013.01); *A61F 2/82* (2013.01);
(Continued)

(58) Field of Classification Search
CPC .......................... A61F 2/95–2/97; A61F 2/2436
See application file for complete search history.

(56) References Cited

U.S. PATENT DOCUMENTS 5,776,142 A * 7/1998 Gunderson ............... A61F 2/88
606/108
6,013,020 A    1/2000 Meloul et al.
(Continued)

FOREIGN PATENT DOCUMENTS

| EP | 2522315 A1 | 11/2012 |
|---|---|---|
| WO | WO 2011/126690 A1 | 10/2011 |
| WO | WO 2012/036741 A2 | 3/2012 |

OTHER PUBLICATIONS

European Search Report for corresponding EP 15275220, dated Apr. 22, 2016, 8 pages.
(Continued)

*Primary Examiner* — Ryan J. Severson
*Assistant Examiner* — Charles M Wei
(74) *Attorney, Agent, or Firm* — Brinks Gilson & Lione

(57) ABSTRACT

The present invention relates to a deployment handle for a prosthesis delivery device and to a delivery device including such a handle. The handle assembly facilitates the controlled release of a prosthesis from the delivery device, while ensuring that various deployment steps are performed in a particular sequential order. The handle assembly comprises a main handle and a second handle which is rotatably and/or longitudinally moveable relative to the main handle. The second handle has an initial position on the main handle such that it prevents access to, and premature manipulation of, a proximal stent release mechanism, until the stent graft has been at least partially unsheathed.

20 Claims, 29 Drawing Sheets

(51) Int. Cl.
*A61F 2/82* (2013.01)
*A61F 2/95* (2013.01)

(52) U.S. Cl.
CPC ............ *A61F 2002/9505* (2013.01); *A61F 2002/9517* (2013.01); *A61F 2002/9665* (2013.01)

(56) References Cited

U.S. PATENT DOCUMENTS

| | | | |
|---|---|---|---|
| 6,402,760 B1* | 6/2002 | Fedida | A61F 2/95 604/528 |
| 7,381,216 B2* | 6/2008 | Buzzard | A61F 2/95 606/108 |
| 7,985,250 B2* | 7/2011 | Kaufmann | A61F 2/95 623/1.11 |
| 8,262,718 B2 | 9/2012 | Chuter et al. | |
| 8,303,546 B2 | 11/2012 | Cordeiro et al. | |
| 8,475,514 B2* | 7/2013 | Hartley | A61F 2/95 623/1.11 |
| 8,523,933 B2* | 9/2013 | Nabulsi | A61F 2/95 623/1.11 |
| 9,173,756 B2 | 11/2015 | Hopkins et al. | |
| 9,326,874 B2* | 5/2016 | Parker | A61F 2/95 |
| 2004/0006380 A1* | 1/2004 | Buck | A61F 2/966 623/1.11 |
| 2004/0138734 A1 | 7/2004 | Chobotov et al. | |
| 2005/0027306 A1 | 2/2005 | Krivoruchko et al. | |
| 2005/0154443 A1 | 7/2005 | Linder et al. | |
| 2005/0273151 A1* | 12/2005 | Fulkerson | A61F 2/966 623/1.11 |
| 2010/0036472 A1* | 2/2010 | Papp | A61F 2/95 623/1.11 |
| 2010/0274227 A1 | 10/2010 | Khairkhahan et al. | |
| 2011/0251664 A1* | 10/2011 | Acosta De Acevedo | A61F 2/07 623/1.11 |
| 2011/0257719 A1* | 10/2011 | Argentine | A61F 2/95 623/1.11 |
| 2011/0288558 A1* | 11/2011 | Nimgaard | A61F 2/95 606/108 |
| 2012/0046652 A1 | 2/2012 | Sokel | |
| 2013/0013049 A1 | 1/2013 | Melsheimer et al. | |
| 2013/0338787 A1* | 12/2013 | Hopkins | A61F 2/95 623/23.7 |
| 2015/0238339 A1* | 8/2015 | Fargahi | A61F 2/966 623/1.12 |
| 2016/0158010 A1* | 6/2016 | Lim | A61F 2/2439 623/1.11 |
| 2016/0184097 A1* | 6/2016 | Lim | A61F 2/2439 623/1.11 |
| 2016/0199206 A1* | 7/2016 | Lim | A61F 2/2439 623/1.11 |

OTHER PUBLICATIONS

Chuter, Timothy A. et al., "Modular branched stent graft for endovascular repair of aortic arch aneurysm and dissection", Journal of Vascular Surgery, Oct. 2003, pp. 859-863.
Examination Report for European Application No. 15193071.6, dated Apr. 24, 2018, 4 pages.

* cited by examiner

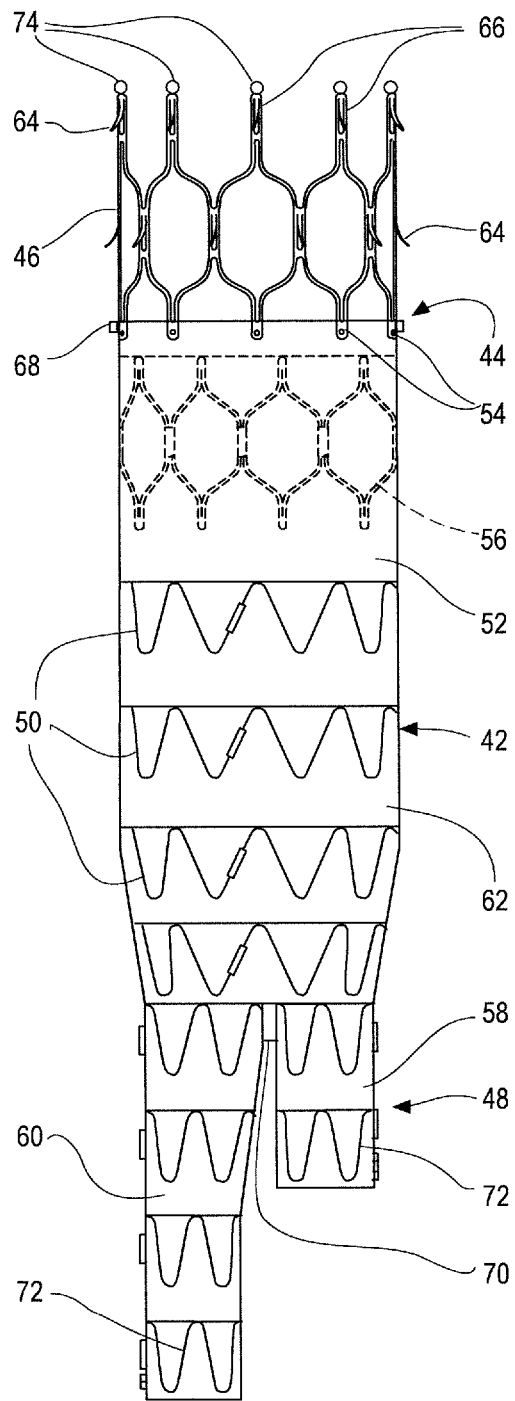

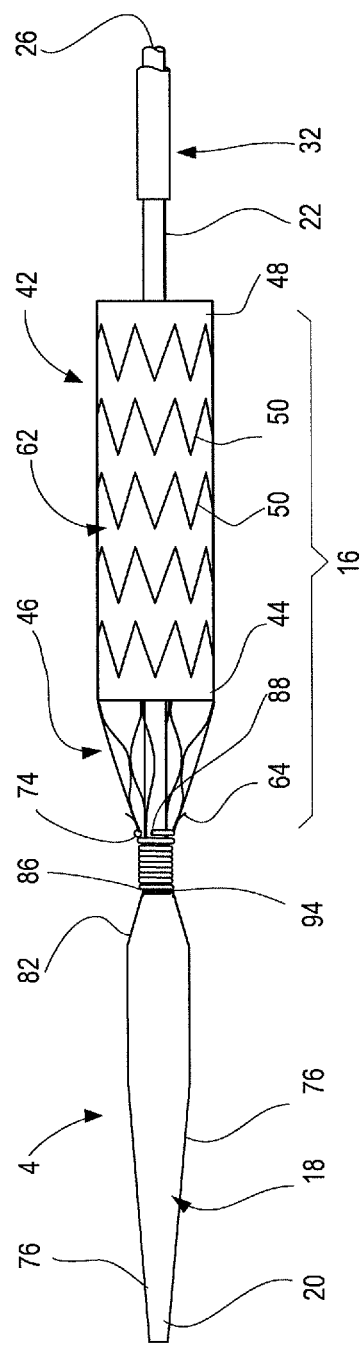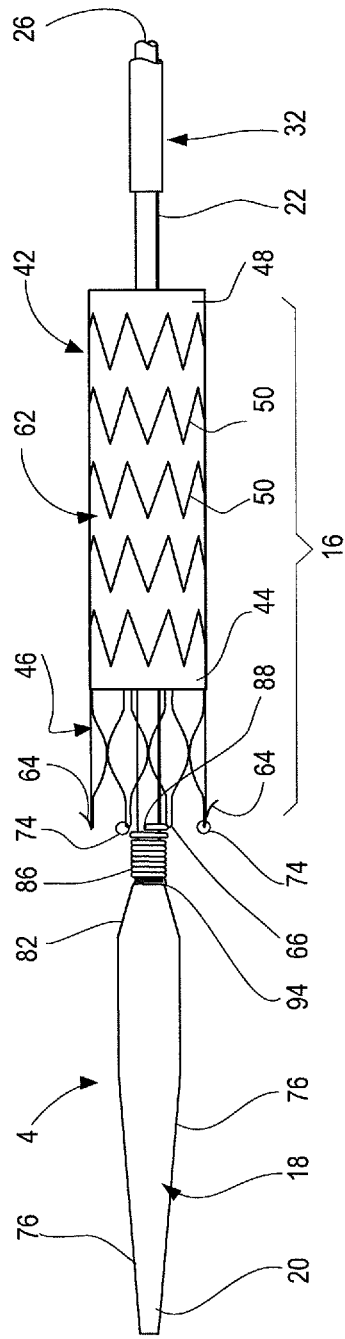

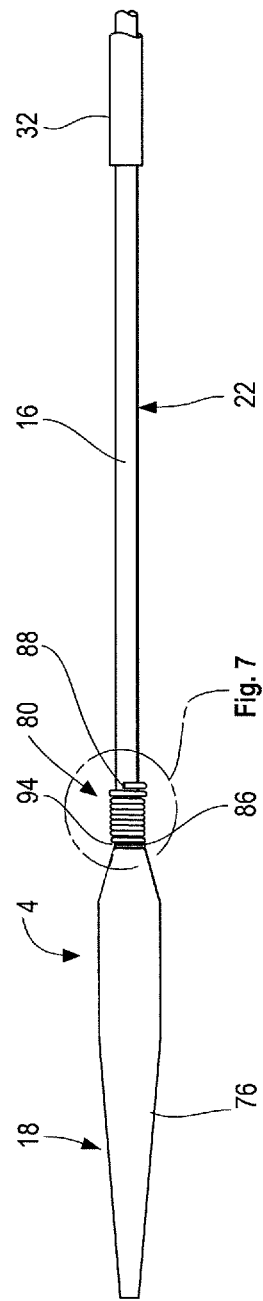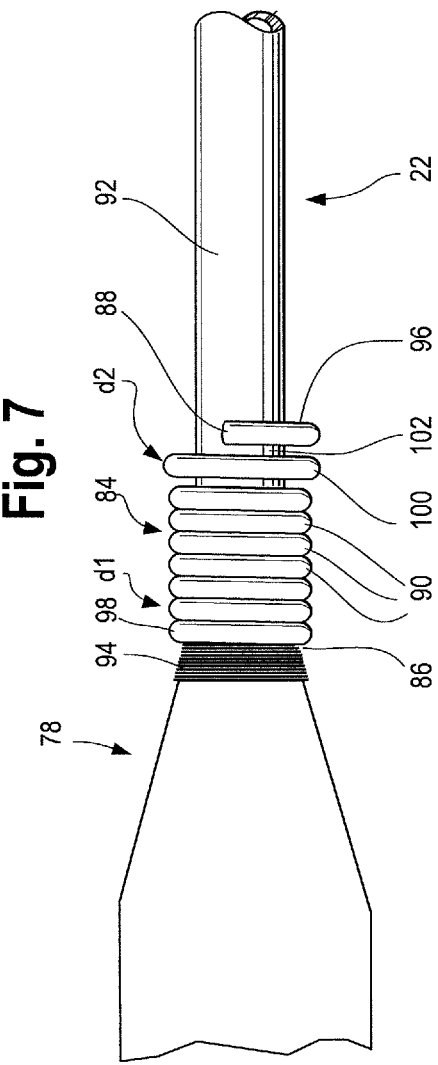

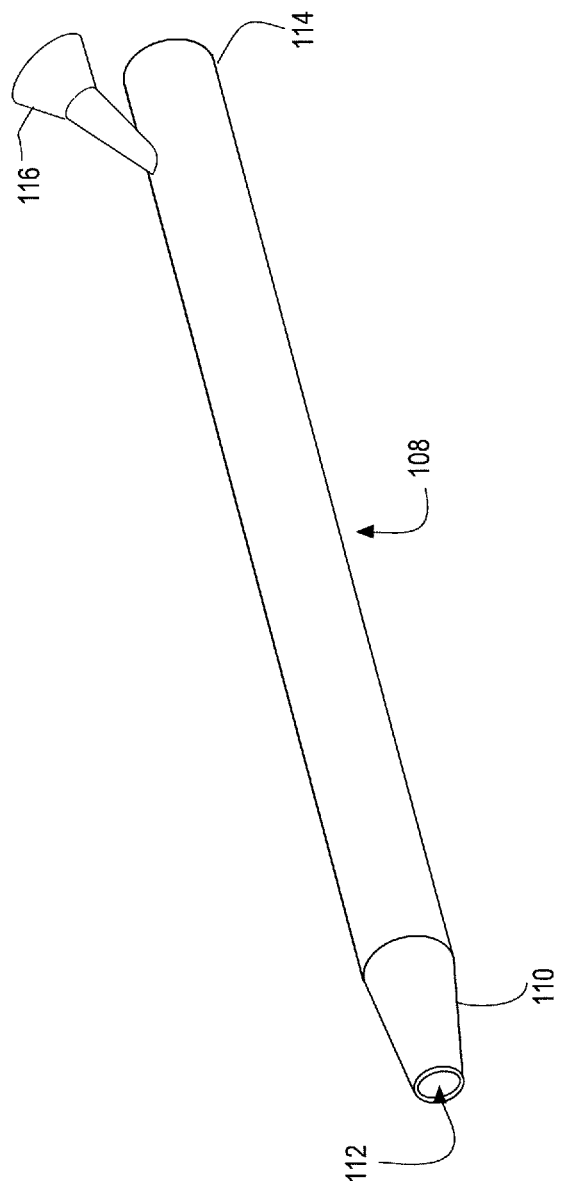

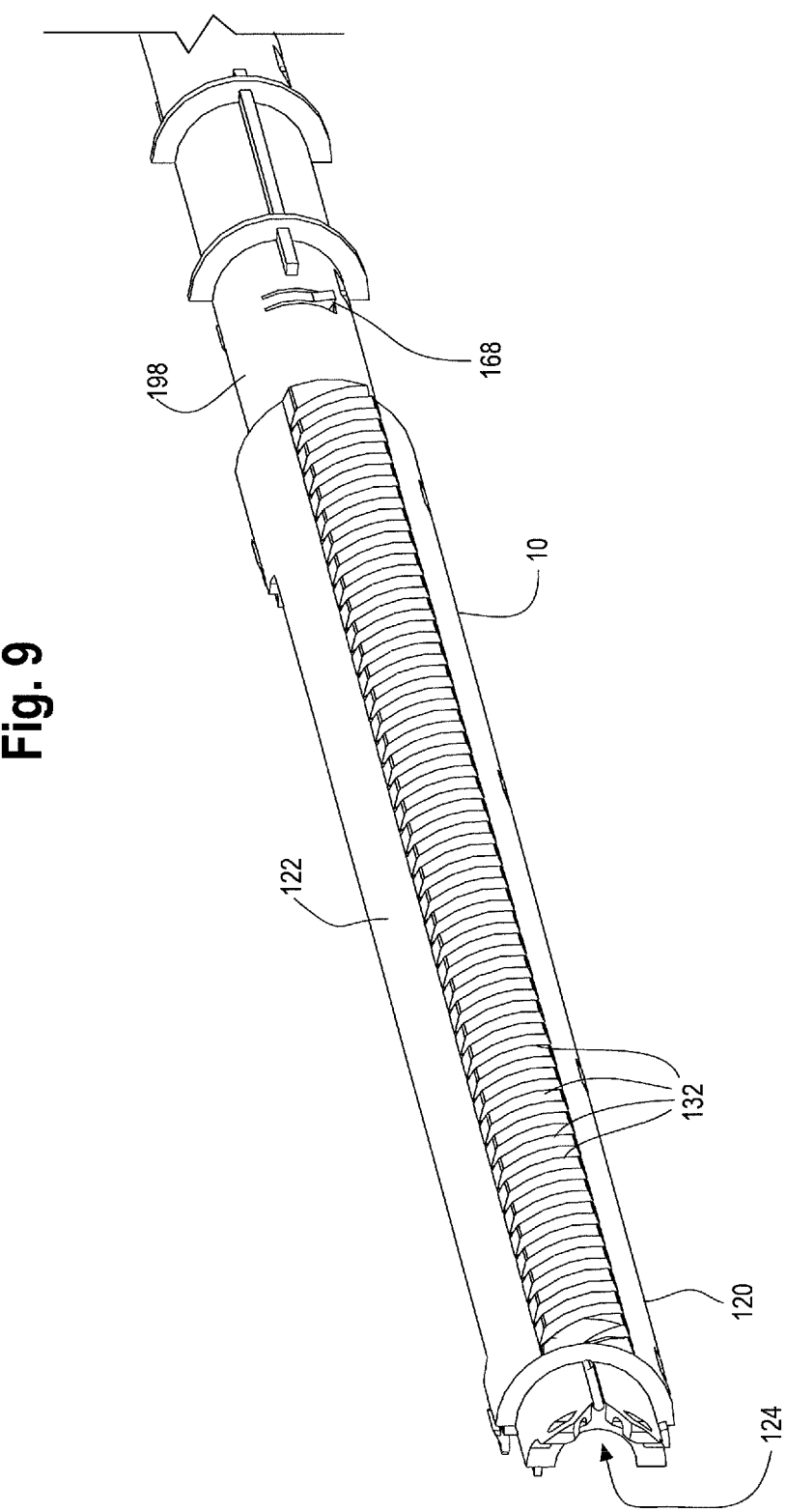

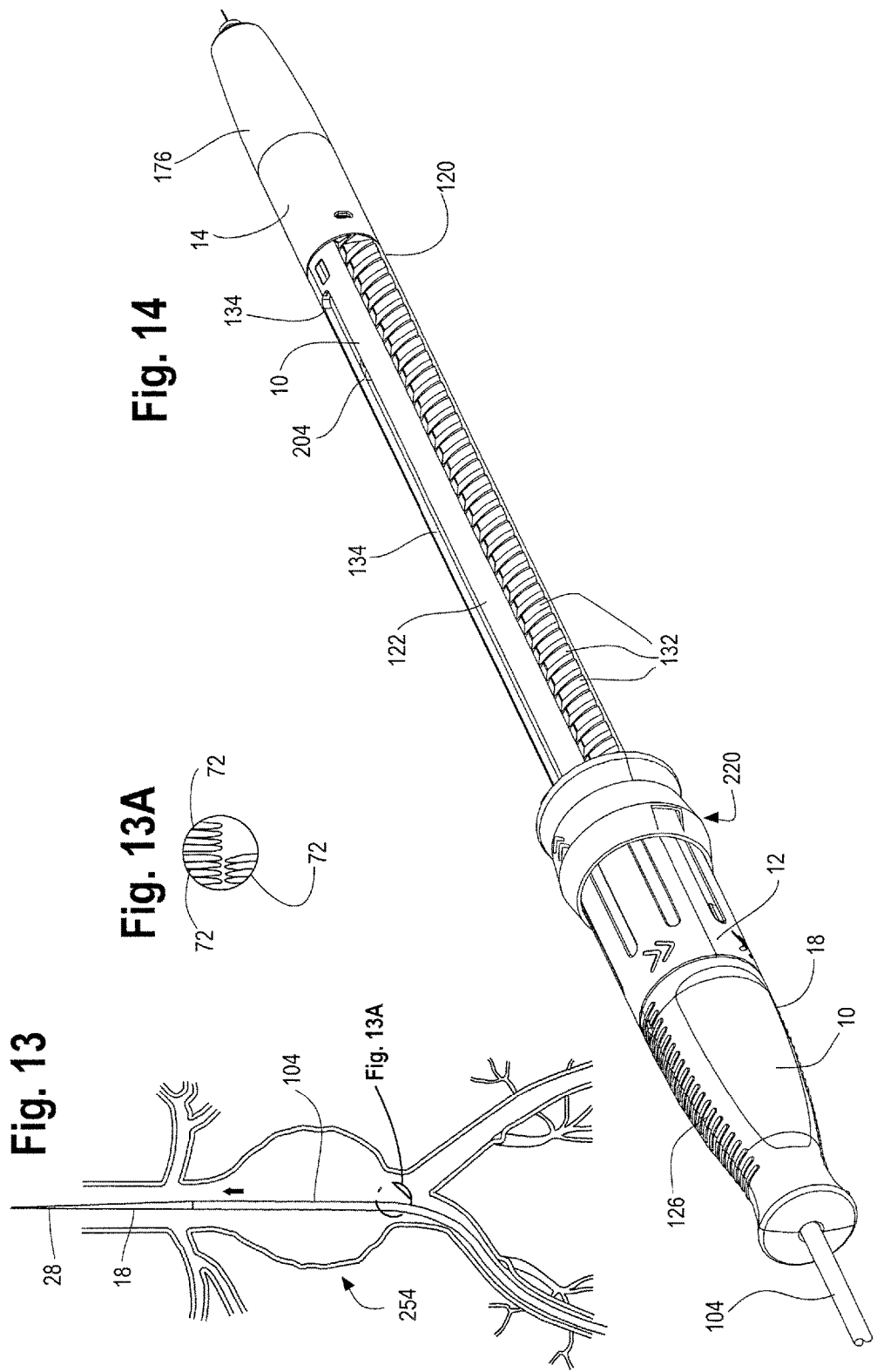

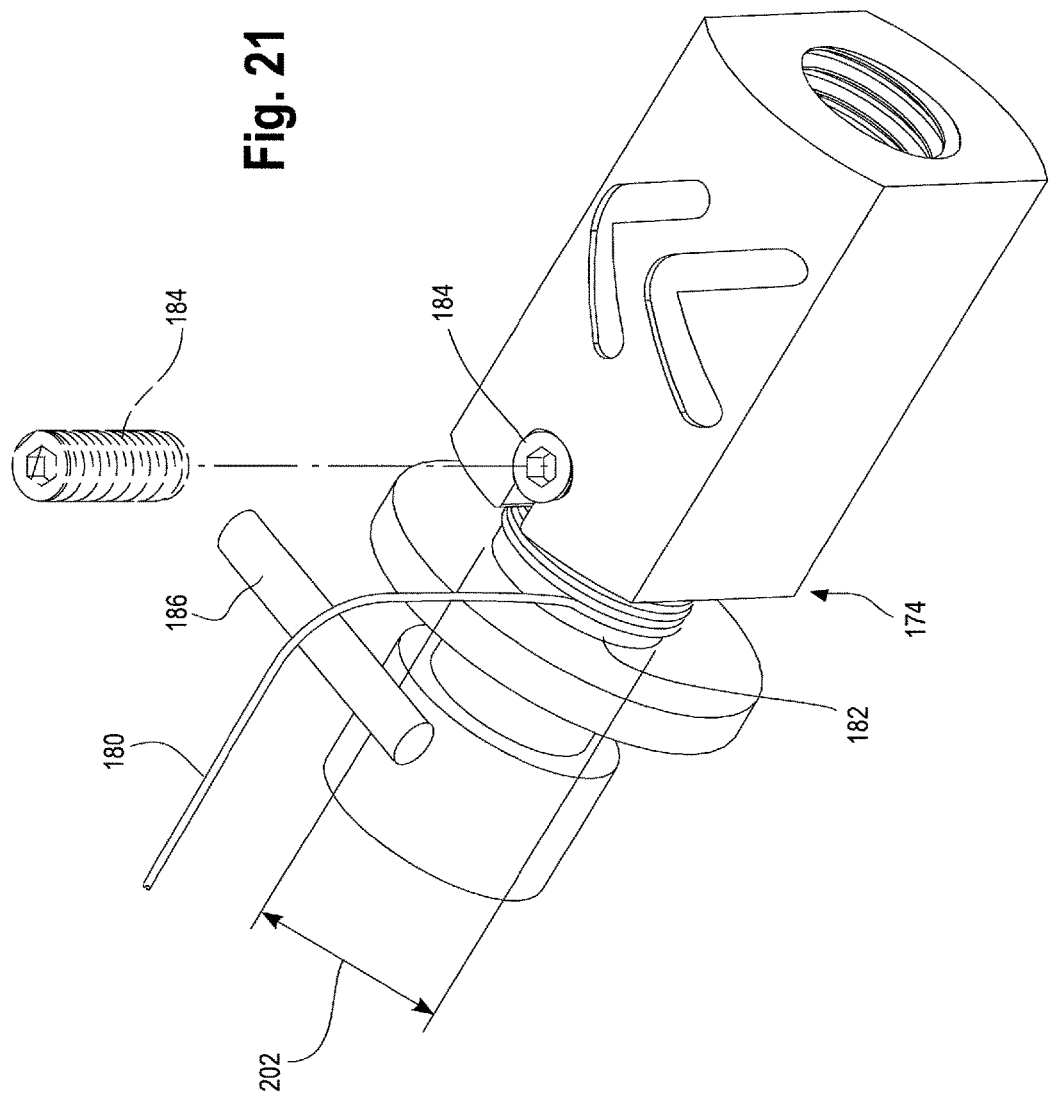

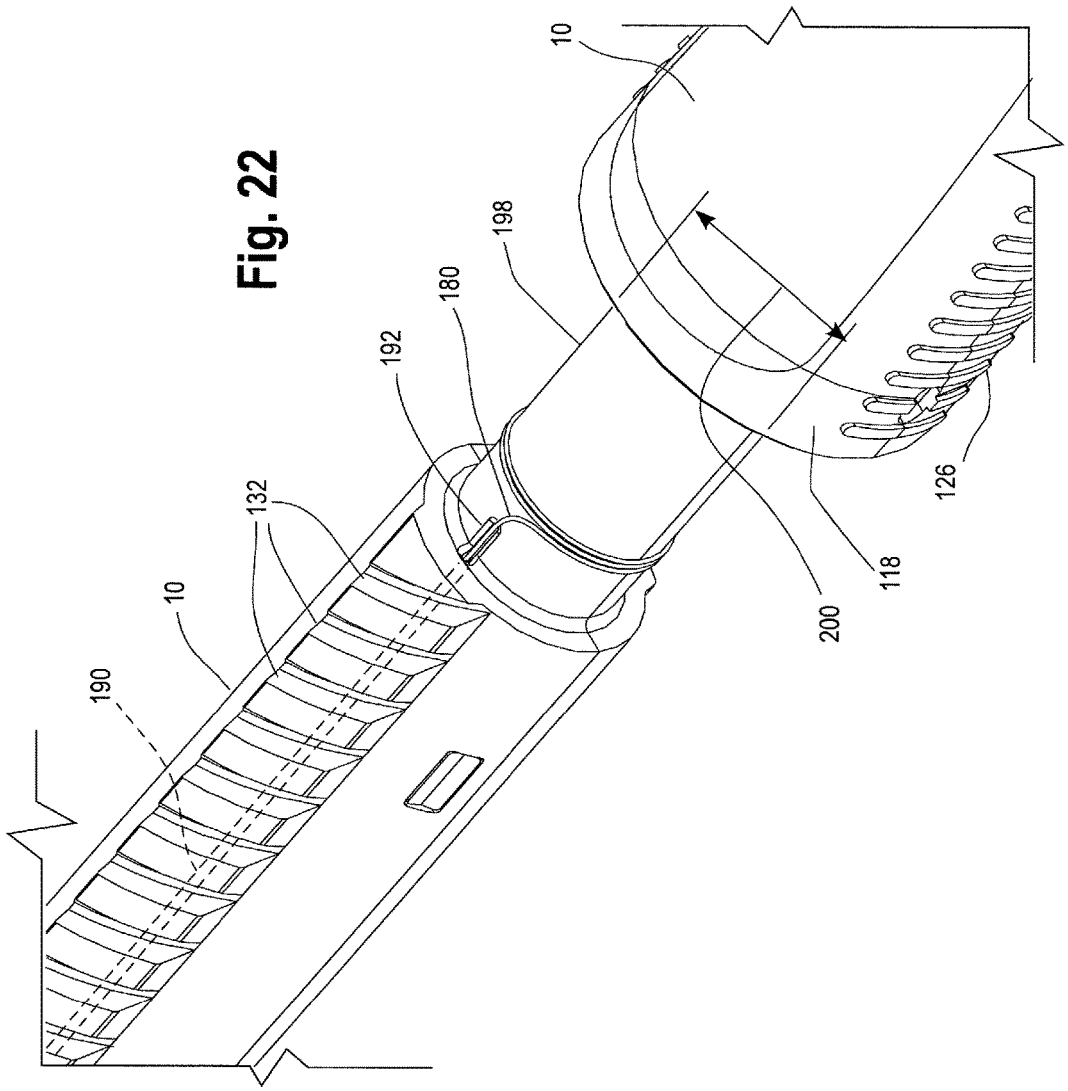

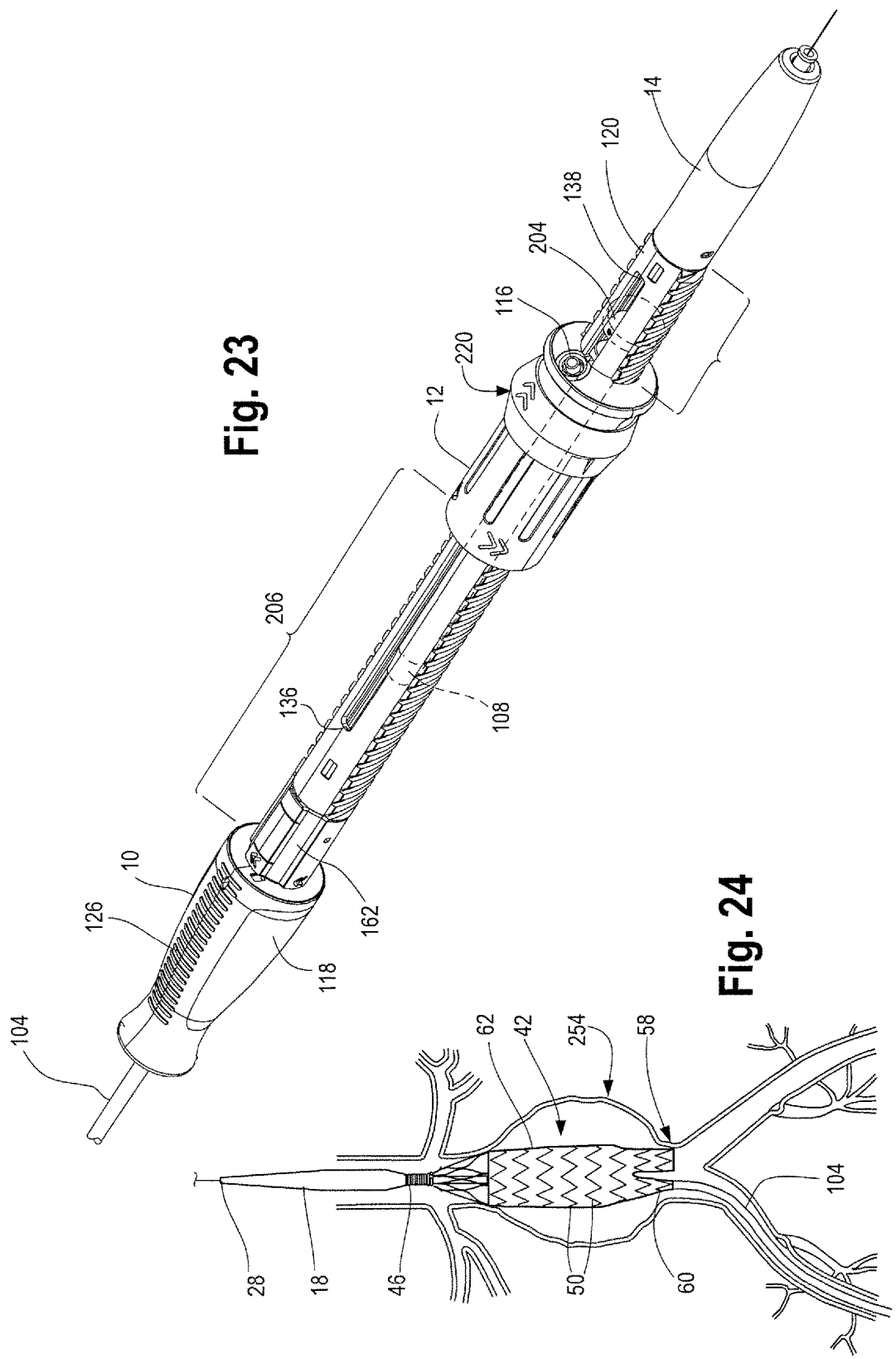

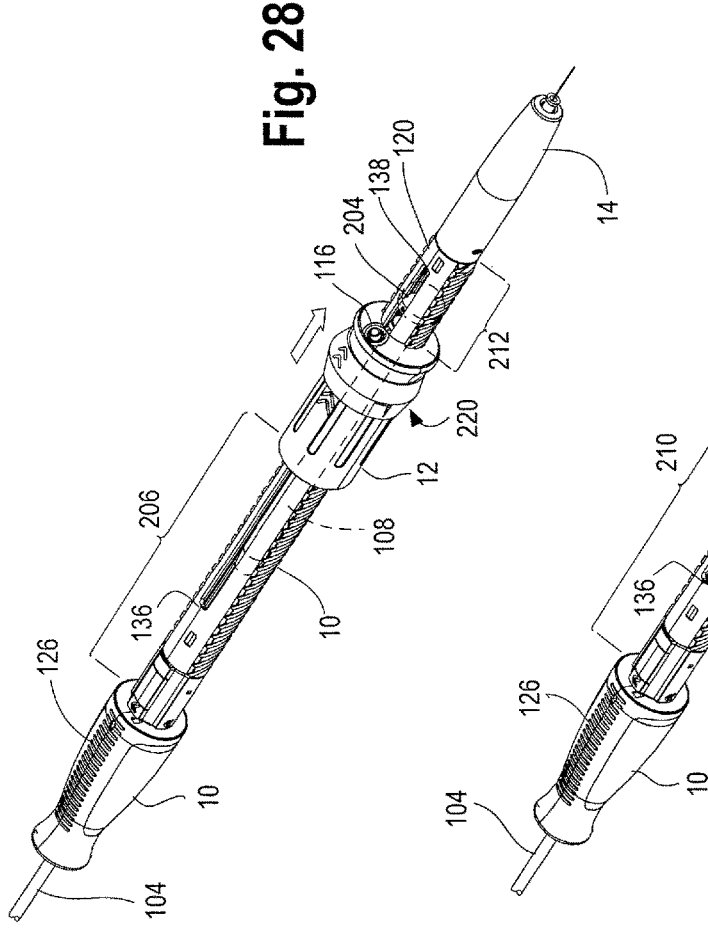
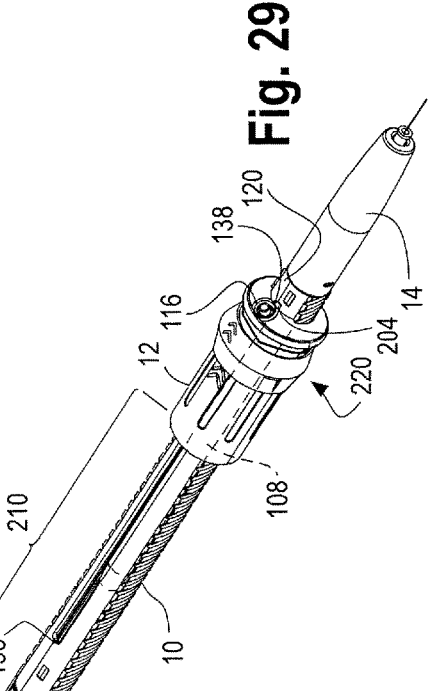
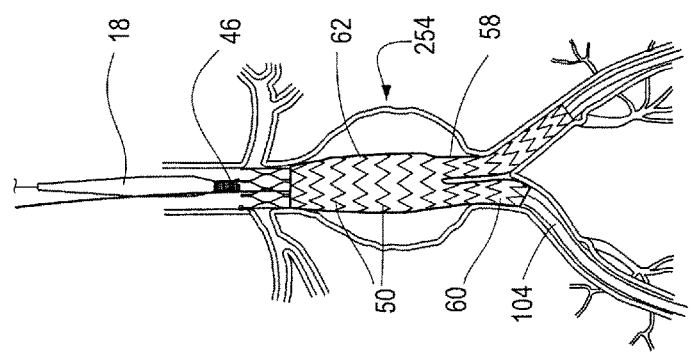

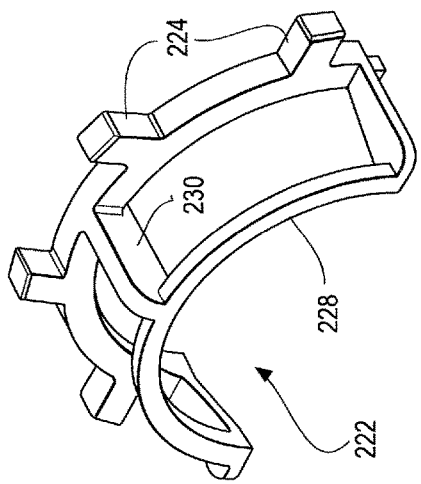
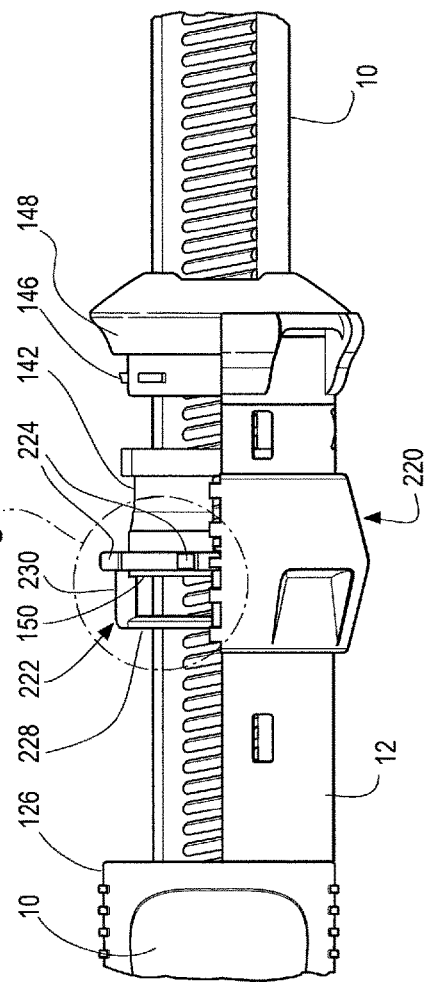
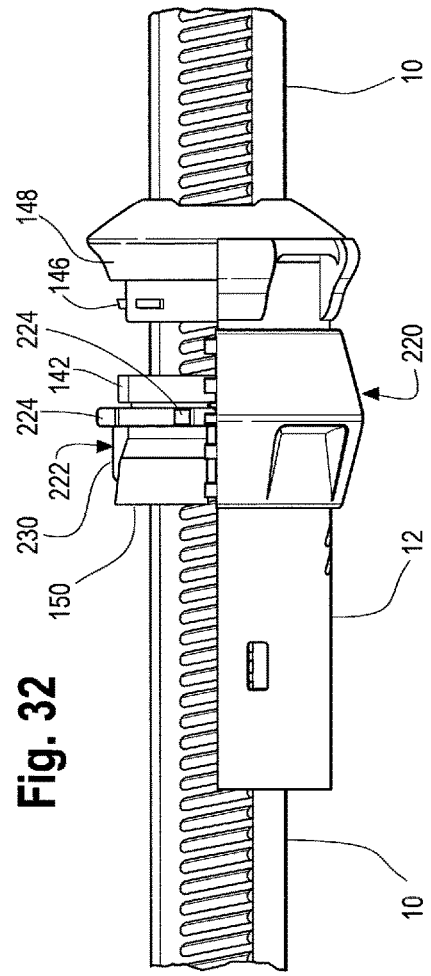

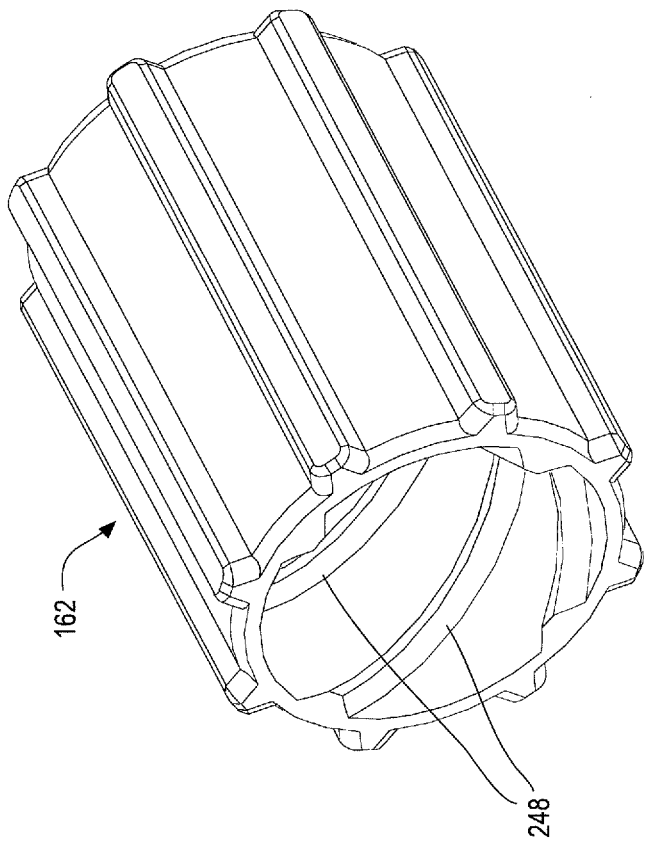

DEPLOYMENT HANDLE FOR A PROSTHESIS DELIVERY DEVICE

RELATED APPLICATIONS

The present patent document claims the benefit of priority to U.S. Provisional Patent Application No. 62/074,766, filed Nov. 4, 2014, and entitled "Deployment Handle For A Prosthesis Delivery Device," the entire contents of each of which are incorporated herein by reference.

TECHNICAL FIELD

The present invention relates to a deployment handle for a delivery device for a prosthesis such as a stent graft, and to a delivery device including such a handle.

BACKGROUND

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable medical device by means of a catheter, often intraluminally. For example, a stent, stent-graft, vena cava filter or occlusion device may be delivered intraluminally from the femoral artery for deployment. For procedures in which a prosthesis or other medical device is implanted into a patient, the prosthesis to be implanted is normally held on a carrier catheter or cannula of the introducer in a compressed state and then released from the carrier catheter so as to expand to its normal operating state, prior to withdrawal of the catheter from the patient to leave the prosthesis in position. In many devices, the steps to carry out the implantation my occur, for example, first by retracting a retractable sheath to expand or partially expand the prosthesis, and then performing further steps to, for example, release one or both ends of the prosthesis, deploy an anchoring stent, or the like. In most cases, it is desirable that such deployment steps follow a specific order as instructed by the manufacturer of the device, but the user of the device is often not restricted from performing steps out of order, and often may do so. Thus, it is desirable to provide a delivery device having a handle assembly that permits controlled and sequential release and deployment of a prosthesis from the delivery device.

SUMMARY

The present invention relates to a deployment handle assembly for a delivery device for a prosthesis such as a stent graft, to a delivery device including such a handle assembly and a method for deploying a stent graft using a device having such a handle assembly. In one example, a handle assembly for a prosthesis delivery device having a proximal and distal end is disclosed. The handle assembly comprises a main handle having a proximal end and a distal end. A prosthesis release actuation mechanism is disposed at least partially on the main handle and moveable relative to the main handle. A motion translating mechanism is disposed distal to and operatively connected to the prosthesis release actuation mechanism. A prosthesis retention mechanism disposed at the proximal end of the delivery device and operatively connected to the motion translating mechanism. The prosthesis retention mechanism has a prosthesis capture condition and a prosthesis release condition. Movement of the prosthesis release actuation mechanism causes movement of the motion translating mechanism thereby moving the prosthesis retention mechanism from the prosthesis capture condition to the prosthesis release condition.

A prosthesis delivery device is also described. In one example, the delivery device has a proximal end and distal end, and a handle assembly at the distal end. The handle assembly comprises a main handle having a proximal end and a distal end and a prosthesis release actuation mechanism disposed at least partially on the main handle and moveable relative to the main handle. A motion translating mechanism is disposed distal to and operatively connected to the prosthesis release actuation mechanism. A prosthesis retention mechanism is disposed at the proximal end of the delivery device and operatively connected to the motion translating mechanism, The prosthesis retention mechanism has a prosthesis capture condition and a prosthesis release condition. Movement of the prosthesis release actuation mechanism causes movement of the motion translating mechanism thereby moving the prosthesis retention mechanism from the prosthesis capture condition to the prosthesis release condition.

In another example, a method for sequentially releasing a prosthesis from a delivery device is described. The delivery device comprises a rotatable inner cannula extending from a proximal end to a distal end, a prosthesis releasably coupled to the proximal end of the inner cannula, a sheath coaxially disposed about at least a portion of the prosthesis and a delivery handle assembly at a distal end of the delivery device. The delivery handle assembly comprises a main handle, a second handle disposed at least partially on the main handle and at least one of circumferentially and longitudinally moveable relative to the main handle and a prosthesis release actuation mechanism disposed at least partially on the main handle. In one example, the method comprises manipulating the second handle from a first position on the main handle to a second position on the main handle to retract the sheath thereby exposing at least a proximal end of the prosthesis and to permit actuation of the prosthesis release actuation mechanism. The method further comprises actuating the prosthesis release actuation mechanism to deploy at least the proximal end of the prosthesis and manipulating the second handle from the second position to a third position on the main handle to further retract the sheath to expose a distal end of the prosthesis.

BRIEF DESCRIPTION OF THE DRAWINGS

FIG. 3 is an exemplary stent graft that may be delivered and deployed within the vasculature of a patient.

FIG. 4 is a side view of the proximal end of the delivery device with the proximal stent of a stent graft held in a radially inward contracted configuration on the delivery device by a prosthesis retention mechanism.

FIG. 5 is a side view of the proximal end of the delivery device with the proximal stent of a stent graft deployed in a radially outwardly expanded configuration.

FIG. 6 is a side view of the proximal end of the delivery device.

FIG. 7 is an enlarged view of FIG. 6 showing one example of a stent graft attachment and release mechanism at the proximal end of the delivery device.

FIG. 8 is a front perspective view of a sheath connector component of the handle assembly.

FIG. 9 is a perspective view of a portion of the main handle of the handle assembly.

FIG. 13 illustrates the delivery device being tracked to a desired location within a patient's vasculature during delivery and deployment of a stent graft.

FIG. 13A is an enlargement of the distal end of a stent graft carried on the delivery device with the stents in a radially inward contracted configuration under a sheath.

FIG. 14 is a perspective view of one example of the handle assembly.

FIG. 21 is an enlarged perspective view of one example of a distal suture drum.

FIG. 22 is an enlarged perspective view of the proximal end of one example of the handle assembly with a suture wrapped about a portion of the main handle.

FIG. 23 is a perspective view of one example of the handle assembly with the second handle moved distally relative to the first handle to retract the sheath and thereby expose a portion of the stent graft during delivery and deployment.

FIG. 24 illustrates the delivery device within a patient's vasculature with the sheath further retracted to expose the main body of the stent graft and contralateral leg during delivery and deployment of a stent graft.

FIG. 27 illustrates the delivery device within a patient's vasculature with the sheath further retracted to expose the ipsilateral limb.

FIG. 28 is a perspective view of the handle assembly of FIGS. 23 and 26, before the ipsilateral limb has been deployed.

FIG. 29 is a perspective view of the handle assembly with the second handle fully retracted to effect deployment of the ipsilateral limb.

FIG. 31 is a side view of one example of a nut and a sleeve retaining the nut into engagement with the main handle.

FIG. 31A shows the sleeve of FIG. 31.

FIG. 32 is a side view of one example of a nut with the sleeve moved distally causing the nut to flare and disengage from the main handle.

FIG. 38 is a perspective view of another example of the proximal suture drum in the handle of FIGS. 33-37.

DETAILED DESCRIPTION

Figure 1:
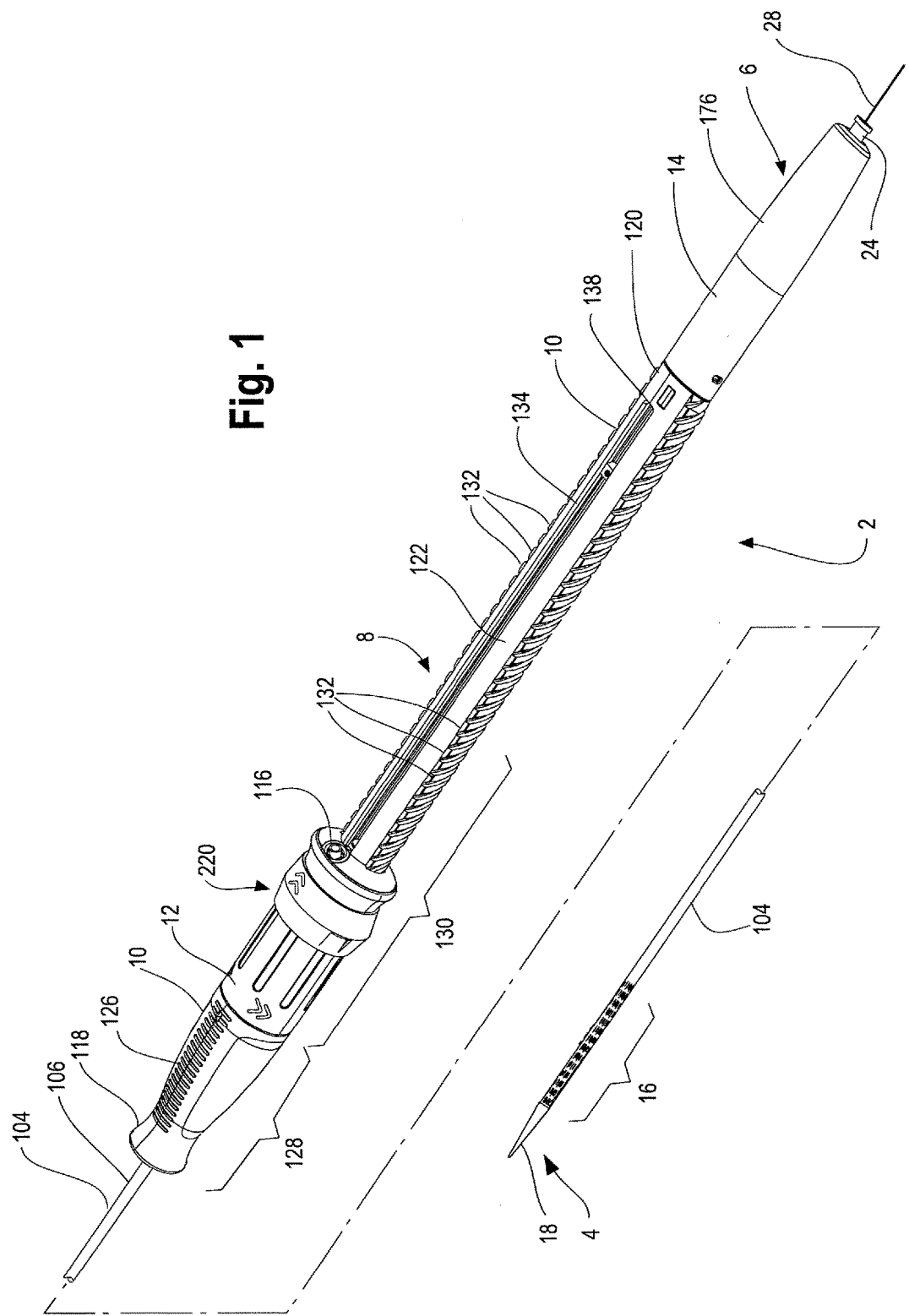
FIG. 1 is a perspective view of a prosthesis delivery device with an example of a handle assembly at the distal end and a prosthesis retained beneath a sheath at the proximal end.

In this description, when referring to a prosthesis delivery device, proximal refers to the part of the delivery device that is furthest from the operator and intended for insertion in a patient's body and distal refers to that part of the delivery device closest to the operator. With regard to the prosthesis, the term proximal refers to that part of the prosthesis that is closest to the proximal end of the delivery device and distal refers to the opposite end of the prosthesis.

In general and described in more detail below with reference to the reference numbers and Figures, the delivery device 2 includes a proximal end 4 and a distal end 6. A handle assembly 8 is located adjacent the distal end of the device. The handle assembly 8, as described in detail below, generally includes first or main handle 10 and a second outer handle 12 and an end cap 14. The main handle 10 is fixed relative to the delivery device 2 and the second handle 12 is disposed on the main handle 10 and is movable longitudinally and/or circumferentially relative to the main handle. Other features of the delivery device 2 and in particular the inventive handle assembly 8 are described more fully below.

As shown in FIGS. 1, 4 and 5, the proximal end 4 of the delivery device 2 includes stent graft retention region 16 and a tapered nose cone dilator 18 having a proximal tip 20. An inner cannula 22 extends the longitudinal length of the delivery device 2, from a distal flush hub 24 at the distal end 6 of the device 2 to the tapered nose cone dilator 18 at the proximal end 4 of the device 2. Inner cannula 22 has an inner lumen 26 which may accommodate a guide wire 28 for tracking the delivery device 2 to a desired position within a patient's vasculature and which may be used for flushing or injection of fluids. The inner cannula 22 may be made of a variety of suitable materials including a flexible material, polymer, metal and/or alloy, for example, nitinol or stainless steel, and may be either straight or have a curve imparted to a portion of it.

A stiffening cannula or positioner 30 may be disposed over at least a portion of the inner cannula 22. The positioner 30 may be constructed from various materials, and in one example, a proximal portion 32 of the positioner which is introduced into the patient may comprise a polymer, sometimes referred to as VRDT (or vinyl radiopaque dilator tubing), plastics, metals, alloys or a combination thereof, whereas a distal portion 34 of the positioner 30 may comprise the same material as the proximal portion 32 of the positioner 30 or it may be a different material including but not limited to plastics, polymers, alloys, metals or a combination thereof, that provide sufficient maneuverability and stiffness to the positioner 30 as necessary and desired. The positioner 30 may extend from a location just distal of the stent-graft retention region 16 coaxial with a length of the inner cannula 22, through the main handle 10, and terminate at a distal end 34 within a stationary collar 36 within the main handle 10. The stationary collar 36 within which the distal end 34 of the positioner 30 is retained may include an insert 38 which is secured to the positioner 30 to help retain the positioner 30 within the stationary collar 36. (See the enlarged view of the distal end of the handle assembly 8 shown in FIG. 19 and FIG. 30). It can also be seen in FIG. 19 that a seal 40, such as an "O" ring or silicone disc may be located adjacent to or just distal of the distal end 34 of the positioner 30 to maintain hemostasis within the main handle 10 and to prevent leakage or back flow of fluids though the positioner 30. For a length of the positioner 30, a stiffening rod (not shown) may be disposed over the inner cannula 22 and/or over the positioner 30 for additional stability and maneuverability.

Referring now to FIG. 3, an exemplary stent graft 42 is shown, which may be deployed in a controlled and sequential manner using the delivery device 2 described herein. The stent graft 42 is carried on the inner cannula 22 at the stent-graft retention region 16 as shown in FIGS. 4 and 5. The stent-graft 42 has a proximal end 44 (that end with the bare stent 46 extending therefrom), a distal end 48, and a series of stents 50 extending the length of the stent-graft 42 and attached to the graft material 52. Extending from the proximal end 44 of the stent-graft 42 is an exposed anchoring stent 46. Anchoring stent 46 is attached to the graft material 52 by, for example, suturing the distal apices 54 of the anchoring stent 46 to the graft material. Next, adjacent the anchoring stent 46 is sealing stent 56. Sealing stent 56 may be internal or external to the graft material 52. A series of body stents 50 also are attached to the graft material 52 and may be sutured to the graft material or held to the graft material in other known ways. The series of body stents 50 may be internal or external to the graft 42, or both. As shown in FIG. 3, sealing stent 56 is internal and body stents 50 are external to the graft material 52.

Anchoring stent 46 may have one or more barbs 64 for attaching the stent-graft 42 to a body vessel. Barbs 64 may be at or near the proximal apices 66 of the anchoring stent 46 and/or be located at some midpoint along the anchoring stent 46. One or more of the proximal apices 66 may include an opening or aperture formed therein, or as shown in FIGS. 3, 4 and 5, a suture loop, aperture or "lollipop" 74 may extend proximally from one or more of the proximal apices. The suture loops 74 are described in further detail below with reference to FIGS. 4 and 5. Radiopaque markers 68 may be placed on various parts of the stent graft 42 and the device 2, including the proximal end 44, along one or both limbs 58, 60, at the bifurcation 70, or other places.

Figure 25:
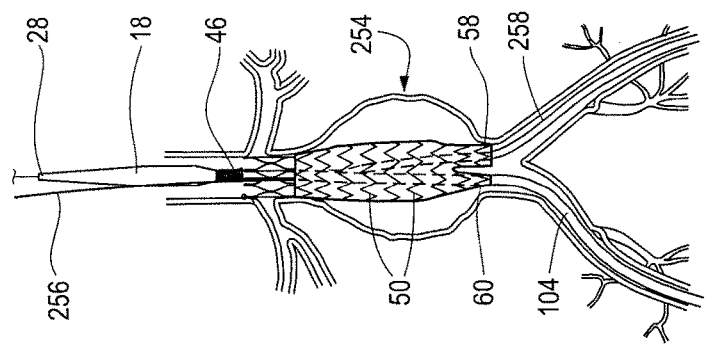
FIG. 25 illustrates the delivery device within a patient's vasculature and the stent graft partially deployed, with a leg extension graft being tracked into the contralateral leg of the stent graft.

As shown in FIG. 3, stent-graft 42 is bifurcated having two limbs 58, 60 extending from the tubular main body 62. One of the limbs 58 may be shorter than the other limb 60, or both may be the same length. As described herein, the shorter limb 58 may be referred to as the "contralateral limb" or "contralateral leg" while the longer limb 60 may be referred to as the "ipsilateral limb" or "ipsilateral leg." Limbs 58 and 60 may also have a series of stents 72 along their length, either or both internal and external. Although FIG. 3 shows a bifurcated stent-graft 42, the stent-graft also may be a single non-bifurcated tube as shown in FIGS. 4 and 5 and/or the stent graft may have one or more fenestrations formed in the graft material 52 and/or one or more side branches or arms or leg extension stent grafts extending therefrom. In one non-limiting example, FIG. 25 shows a leg extension graft 258 extending from the contralateral leg 58).

An exemplary coupling of the stent graft 42 to the delivery device is shown in FIGS. 4-6. More specifically, FIGS. 4-6 illustrate a proximal end portion 4 of the delivery device 2, and one non-limiting example of an attachment and release mechanism for the proximal end 44 of a stent graft 42 that can be operated using the handle assembly 8 described herein. FIG. 4 shows the tapered nose cone dilator 18 having a proximal tip 20 and a reverse distal taper 78 at its distal end. The nose cone surface presents a smooth tapered surface 76 to facilitate entry into and movement through a body vessel. Nose cone dilator 18 may include radiopaque material or be equipped with a radiopaque marker (not shown) to facilitate visualization of the nose cone dilator 18 in use.

As shown in FIG. 6, an exemplary prosthesis attachment and retention mechanism 80 (sometimes referred to herein as a "coiled member" or "coil" or "helix") is disposed at or near the distal end 82 of the nose cone 18 and on the inner cannula 22. In a non-limiting example, as shown in enlarged view in FIG. 7, the attachment and release mechanism 80 comprises a coiled member or helix 84 having a proximal end 86, a distal end 88, and a plurality of turns 90 disposed there between. However, other attachment and release mechanisms may also be used to releasably attach the proximal end of the stent graft to the delivery device including one or more trigger wires, diameter reducing ties and the like as will be recognized by one of skill in the art.

In one non-limiting example, the proximal end 86 of the coiled member 84 is secured to the outer surface 92 of the cannula 22 using a suitable attachment mechanism 94, such as a solder, weld, mechanical attachment, friction fit, crimp, or combination of these or other techniques. Accordingly, the proximal end 86 of the coiled member 84 cannot move relative to the outer surface 92 of the inner cannula 22. The proximal end 86 of the coiled member 84 comprises a first diameter d 1, which may be approximately the same diameter, or slightly greater than, an outer diameter of the cannula 22.

The distal end 88 of the coiled member 84 is unsecured relative to the outer surface 92 of the inner cannula 22, as shown in FIG. 7. The distal end 88 of the coiled member 84 may comprise a second diameter d 2 which is greater than the first diameter d 1 of the proximal end 86 of the coiled member 84. There is a separation or gap 96 between the distal end 88 of the coiled member 84 and the outer surface 92 of the cannula 22, as best seen in FIG. 7.

The plurality of turns 90 are divided into a proximal series of turns 98, which have the first diameter d 1, and a distal series of turns 100, which have the second diameter d 2. The proximal series of turns 98 may be disposed in close proximity or abutting one another, as depicted in FIG. 7. By contrast, the distal series of turns 100 may be spaced apart from one another a greater distance than the proximal series of turns 98. In FIG. 7, the distal series of turns 100 are spaced apart a predetermined distance denoted by spacing 102.

As shown in FIGS. 4 and 5, prosthesis, such as stent graft 42, is disposed on the inner cannula 22 at the proximal end 4 of the delivery device 2 at stent graft retention region 16. The stent graft 42 has an uncoupled or released state in which the graft is positioned coaxially over the inner cannula 22 with the proximal end 44 of the stent graft 42 in longitudinal proximity relative to the distal end 88 of the coiled member 84, as shown in FIG. 5. During assembly, one or more proximal apices 66 and/or one or more apertures or loops 74 that are coupled to the proximal apices 66 of the stent 46 are threaded around the distal end 88 of the coiled member 84 one at a time, preferably until all of the proximal apices 66 and/or loops 74 are coupled to the coiled member 84. Such coupling may be achieved by rotating the inner cannula 22 until the proximal end of the stent 46 is sufficiently compressed in a radially inward direction, such that it is in a captured condition, as depicted in FIG. 4. A gap 96 between the distal end 88 of the coiled member 84 and the outer surface 92 of the inner cannula 22 permits positioning of the proximal apices 66 or loops 74 in the series of turns at the distal end 88 of the coiled member 84. This type of attachment system of the proximal stent to the delivery system is more fully described in U.S. application Ser. No. 13/796,395 (filed Mar. 12, 2013) which is incorporated by reference in its entirety.

The loops 74 are further accommodated within a spacing 102 between the distal series of turns 100. The loops 74 preferably are coupled to the coiled member 84 in a manner in which at least one suture loop 74 (or apex 66) is positioned around at least one full turn of the distal series of turns 100, and preferably around at least 1.5 turns at the distal end 88 of the coiled member 84, thereby reducing the likelihood of inadvertent uncoupling of the loops 74 from the coiled member 84.

The coupling shown in FIG. 4 captures or secures the stent 46 to the cannula 22 via the coiled member 84 in a manner that may subsequently facilitate insertion of the subassembly comprising the inner cannula 22 and the stent graft 42 into an outer sheath 104, such as sheath 104 described below. As will be apparent, the outer sheath 104 is configured to radially restrain other regions of the stent graft 42 for delivery to a target site within a patient's anatomy.

The loops 74 may be coupled to every other proximal stent apex 66 as shown in FIG. 5 to restrain the stent 46 during delivery. In such a case, the loops 74 are not coupled to every other proximal apex 66, which may comprise barbs 64. By restraining the alternating proximal apices 66 using the loops 74 coupled to the coiled member 84, the adjacent second proximal apices 66 also may be indirectly pulled in a radially inward direction during delivery. The configuration of the stent 46 facilitates the indirect compression of the adjacent second proximal apices 66. Since only selected ones of the proximal apices 66 are restrained during delivery, the number of apertures or loops 74 may be reduced. This type of attachment system of the proximal stent to the delivery system is more fully described with reference to FIGS. 4 and 5 of U.S. application Ser. No. 13/796,395 (filed Mar. 12, 2013) which description and figures, and in particular FIGS. 1, 2, 4 and 5 are hereby incorporated by reference in their entirety.

As shown in FIG. 1, a longitudinally slideable and retractable sheath 104 extends along the length of the delivery device 2 from the main handle 10 to the nose cone dilator 18. The sheath 104 is configured to cover and assist in retaining a prosthesis, such as a stent or stent graft 42, in a radially inwardly compressed, low-profile configuration during delivery of the prosthesis to a target site within a patient's anatomy. The distal end 106 of the sheath 104 is connected within the main handle 10 by a sheath connector 108, which is shown in detail in FIG. 8. In one example, the distal end 106 of the sheath 104 may be slightly flared to facilitate attachment of the sheath 104 to a correspondingly shaped tapered proximal end 110 of the sheath connector 108. The distal end 106 of the sheath 104 may be secured to the proximal end 110 of the sheath connector 108 by a friction fit, threaded engagement, adhesives or other attachment mechanisms or combination thereof. The sheath connector 108 has at least one lumen 112 extending from its proximal end 110 to its distal end 114, which allows for sheath connector 108 to travel or slide longitudinally along the positioner 30. The sheath connector 108 also includes a sheath flush port 116, comprising a one way valve that communicates with the sheath connector lumen 112 to allow sheath flushing prior to introduction into the vasculature. An O-ring or silicone disc at the distal end of the sheath connector lumen 112 and a seal within the sheath flush port 116 prevents unintended back flow or leakage of fluid through the sheath connector 108 and flush port 116.

Figure 2:
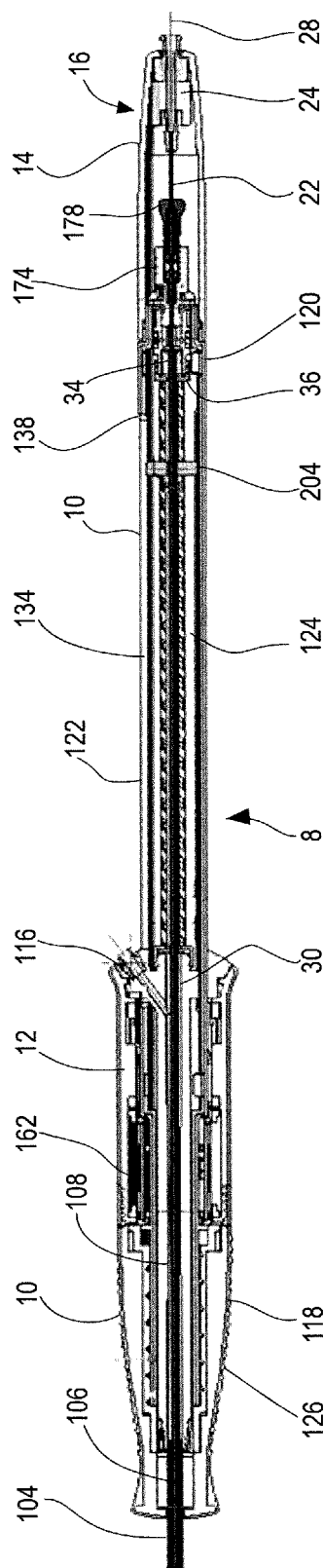
FIG. 2 is a side cross sectional view of the handle assembly of FIG. 1.

FIG. 1 shows a rear perspective view of the delivery device 2 with the handle assembly 8 while FIG. 2 illustrates a side cross sectional view of the of the handle assembly 8. As shown, the handle assembly 8 includes a first or main handle 10 and second or outer handle 12. The main handle 10 is fixed relative to the delivery device 2. The second handle 12 is disposed on at least a portion of the main handle 10 and is movable longitudinally and/or circumferentially relative to the main handle 10.

The main handle 10 comprises a proximal end 118 and a distal end 120 with an outer surface or side wall extending therebetween to form a handle interior 124. As will be described below, the handle interior 124 houses additional mechanical components that make up the handle assembly 8. The main handle 10 may be injection molded as a single unitary structure or alternatively, as shown in FIG. 9 the main handle 10 may comprise upper and lower parts or first and second halves that clam shell, lock, snap-fit or are otherwise securable to each other.

The proximal end 118 of the main handle 10 may include a gripping portion 126 for a physician to grip with one hand while manipulating the second handle 12 (such as during sheath retraction during deployment). The gripping portion 126 of the main handle 10 is preferably ergonomically shaped for user comfort, and may be covered in a layer of softer plastic or rubber or have a gripping surface to ensure a stable grip. As shown in FIG. 1, the gripping portion 126 is a proximal portion 128 of the main handle that may have a greater diameter than the remainder of the main handle 10 which has a reduced diameter portion 130 and extends distally behind the gripping portion 126. It is the reduced diameter portion 130 of the main handle 10 upon which the second handle 12 can longitudinally move.

Figure 10:
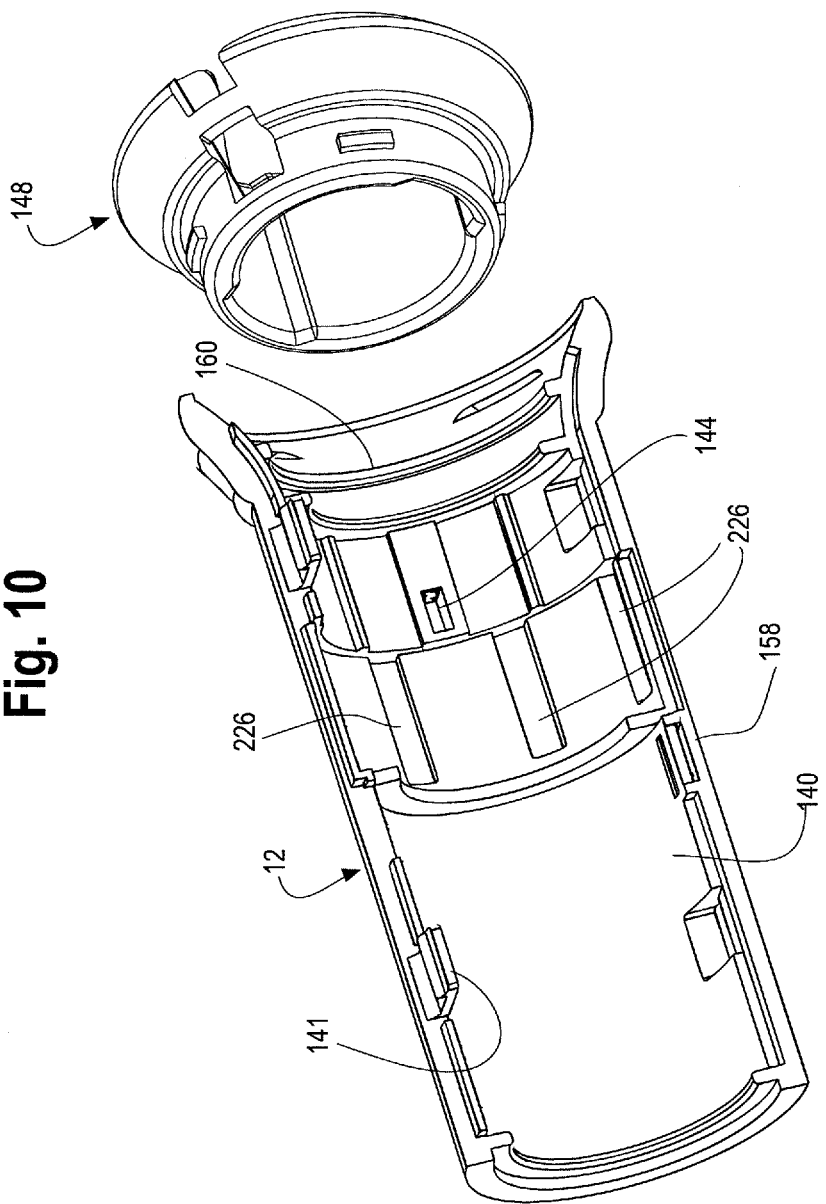
FIG. 10 is a sectional view of the second handle of the handle assembly.

At least a portion of the outer surface 122 of the main handle 10 includes partial or full threads 132 along its outer surface 122, which threads 132 extend distally from a location just distal of the gripping portion 126 to the handle end cap 14. A longitudinal slot 134 having a proximal end 136 and a distal end 138 is formed along a portion of the length of the main handle 10, between the gripping portion 126 and the handle end cap 14. As shown in FIG. 1, the second handle 12 is located on the main handle 10. The second handle 12 may be a generally tubular structure that extends at least partially around the outer surface 122 of the main handle 10. The second handle 12 may be injection molded as a single unitary structure or alternatively, as shown in FIG. 10, the second handle 12 may comprise upper and lower parts or halves that clam shell, lock, snap-fit by snaps 141 or are otherwise securable to each other. The second handle 12 may further include an end cap 148. The end cap 148 may consist of two halves which can be attached together by various mechanisms such as snap fit, friction fit, corresponding engageable protrusions or by adhesives. The second handle 12 mechanically engages with the end cap 148 thereby preventing axial/longitudinal movement between the respective two parts but allows the second handle 12 to rotate independently from the end cap 148. In one example, as shown in FIG. 10, one or more protrusions 160, such as a collar, thread or ring on the inner surface 140 of the second handle 12 may be engageable with a correspondingly shaped collar, protrusion, thread or ring on the end cap 148.

Figure 11:
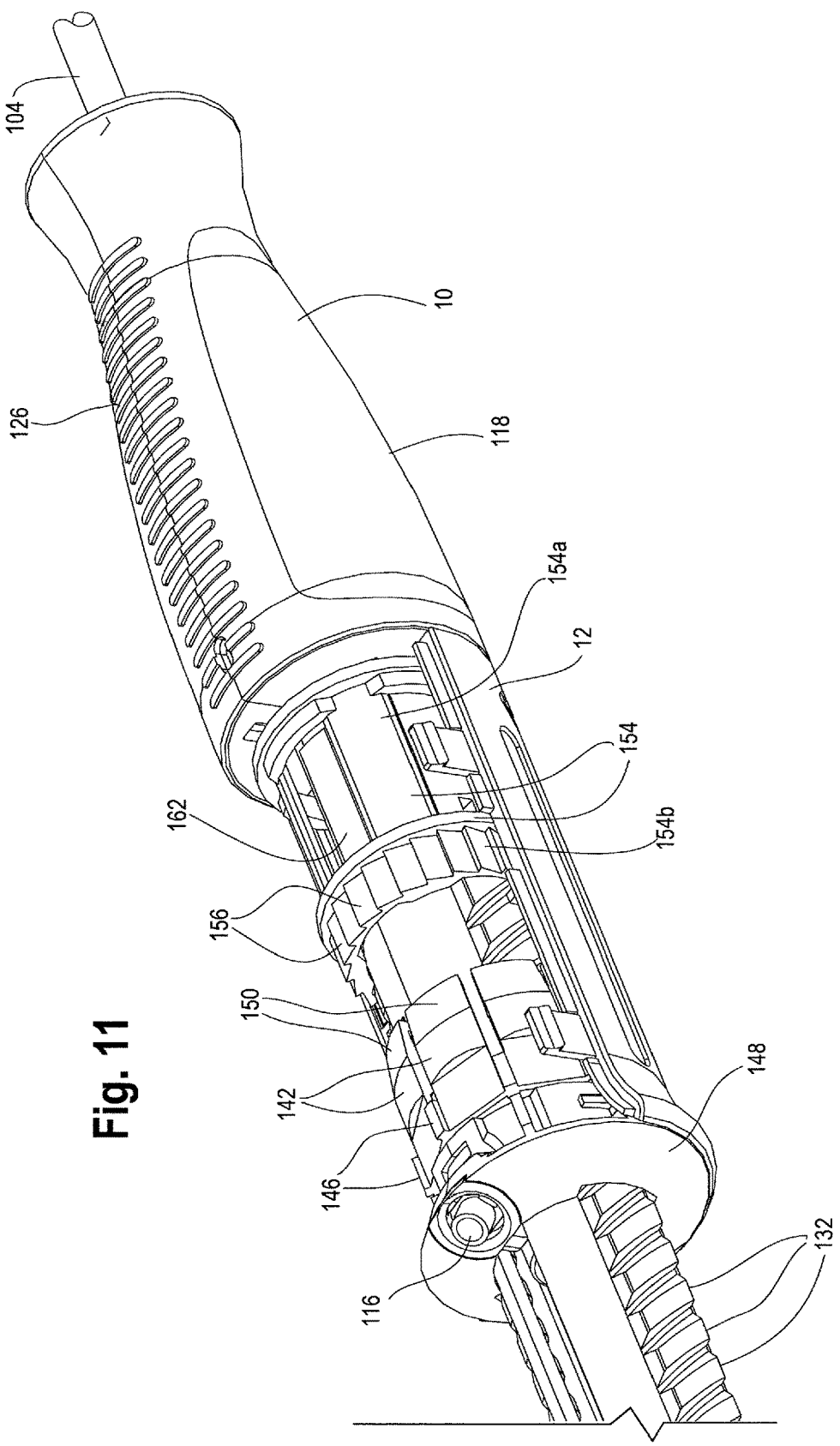
FIG. 11 is an enlarged view of the proximal end of the handle assembly with a portion of the second handle removed.

The inner surface 140 of the second handle 12 may further comprise one or more structures, which engage with a mechanism such as a nut 142. The nut 142 is located within the second handle 12. In one non-limiting example, as shown in FIG. 10, the second handle 12 may comprise an opening or aperture 144 which engages with one or more radial protrusions 146 on the nut 142 (See FIG. 31). As such, at least a portion of the inner surface 140 of the second handle 12 is engaged or otherwise operatively connected with the nut 142. One of skill in the art would recognize that any similar mechanisms or structures that allow the second handle 12 to engage with the nut 142 may be used. As shown in FIG. 11, the nut 142 may be a cylindrical or tubular structure that completely encircles a portion of the main handle 10, or the nut 142 may partially cover or surround the main handle 10. In one example, the nut 142 may be a solid structure, or as shown in FIGS. 11, 12, 31 and 32, a distal end 149 may be a solid structure or ring which encircles a portion of the main handle 10 while a proximal end 150 of the nut 142 may comprise a series of adjacent panels, fingers or flanges that extend proximally from the distal end 149 of the nut 142. As will be described in further detail below, the proximal end 150 of the nut 142 may flare radially outwardly in a neutral or relaxed state. (See FIG. 11 and FIG. 32, for example). In a second radially inwardly compressed state, the inner surface of the nut 142 is configured to engage with an outer surface 122 of the main handle 10. (See FIG. 31, for example.)

Figure 15:
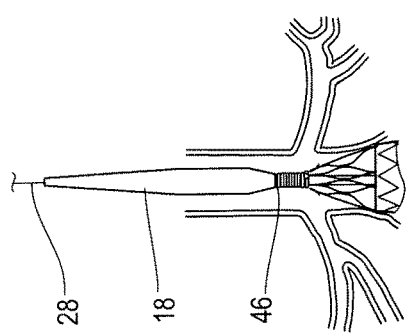
FIG. 15 illustrates the delivery device being tracked to a desired location within a patient's vasculature with the sheath retracted to expose a proximal end of the stent graft during delivery and deployment of a stent graft.
Figure 16:
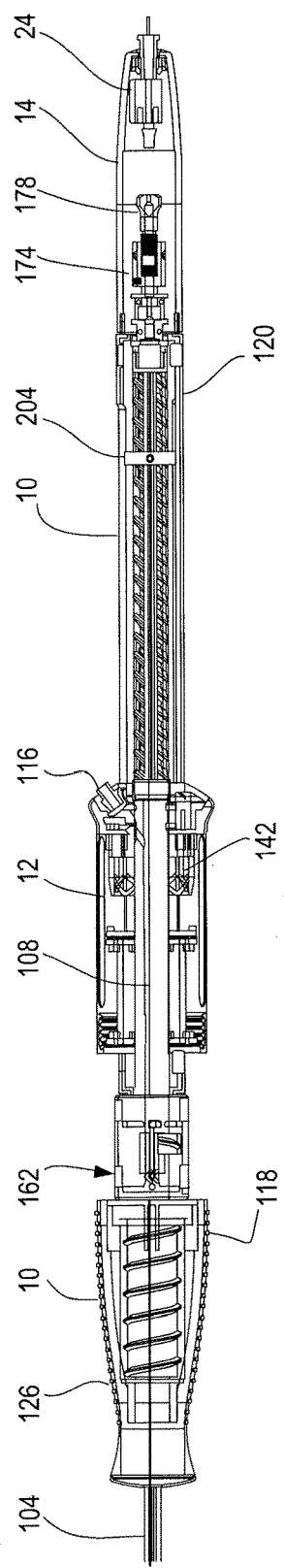
FIG. 16 is a cross sectional view of one example of the handle assembly with the second handle moved distally relative to the main handle to expose a prosthesis release actuation mechanism, or proximal suture drum.

It can be seen in FIGS. 14, 16 and 23, that the second handle 12 may be rotated from its first proximal most position on the main handle 10 (as shown in FIGS. 1 and 14) to a second or an intermediate position (FIG. 16 and FIG. 28, for example) located between the proximal and distal ends 136, 138 of the longitudinal slot 134 formed in the main handle 10. Distal movement of the second handle 12 relative to the main handle 10 requires rotation of the second handle 12 when the inner surface 152 of the nut 142 within the second handle 12 is threadedly engaged with the outer surface 122 of the main handle 10. This threaded engagement necessitates rotation of the second handle 12 to impart longitudinal movement of the second handle 12 relative to the main handle 10. Rotation of the second handle 12 may be desired so as to provide more control and accuracy to the sheath retraction and proximal stent 46 placement and deployment (as shown in FIGS. 15 and 25, for example).

Figure 12:
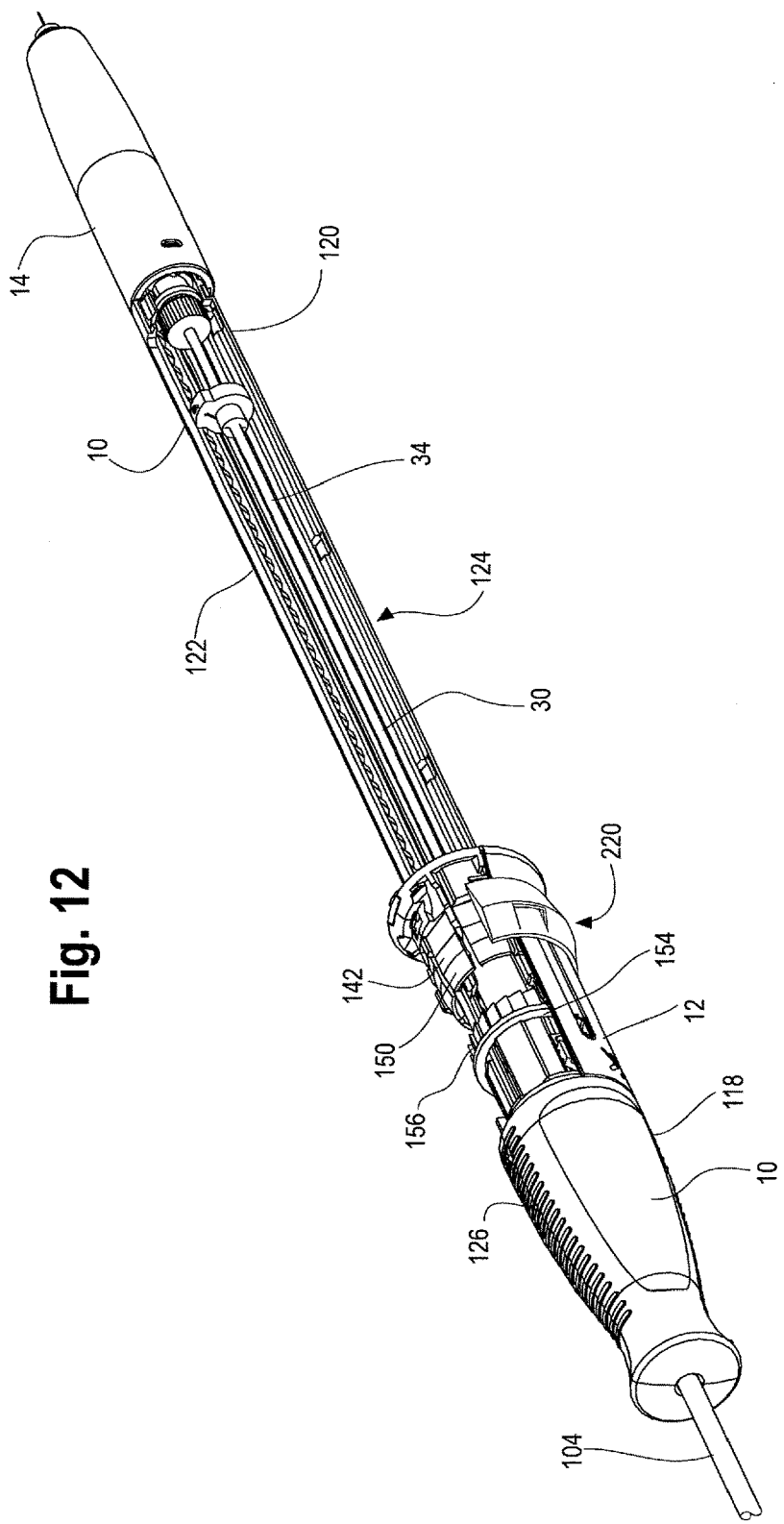
FIG. 12 is a front perspective view of the handle assembly with a portion of the second handle and outer ring removed.

FIGS. 11 and 12 are perspective views of the handle assembly 8 shown with a portion of the second handle 12 removed, showing the second handle 12 in a first, proximal most position on the main handle 10. A ratcheted collar 154 is positioned under the second handle 12. The ratcheted collar 154 may fully or partially surround the main handle 10. As shown in FIG. 11, the ratcheted collar 154 extends distally from the gripping portion 126 of the main handle 10. The ratcheted collar 154 may be molded from a single unitary piece of material or may be multiple separately molded pieces (i.e., a collar portion 154a and a ratchet portion 154b) which are attached together such as by welding or glue. The ratcheted collar 154 may have one or more protrusions or teeth 156 that allow only for unidirectional rotation of the second handle 12. For example, one or more protrusions 158 formed on the inner surface 140 of the second handle 12, or, alternatively a shim 158 positioned in a slot on the interior surface 140 of the second handle 12, as shown in FIG. 10, engage with the ratcheted collar 154, so that the second handle 12 can rotate about the main handle 10 in one direction, while rotation of the second handle 12 about the main handle 10 in the opposite direction is prevented. The ratcheted collar 154 is preferably shaped so that the ratcheted collar 154 does not rotate relative to the main handle 10, but which allows the ratcheted collar 154 to slide longitudinally relative to the main handle 10. For example, the cross sectional shape of the ratcheted collar 154 may be oblong or polygonal, have one or more flat sides or be irregularly shaped so that rotation of ratcheted collar 154 is prevented when the second handle 12 is rotated about the main handle 10, but which allows the ratcheted collar 154 to move longitudinally along the main handle 10 as the second handle 12 is moved distally by the user.

Before use of the delivery device 2 and when the delivery device is tracked to a desired location within a patient's body as shown in FIGS. 13 and 14, the second handle 12 is disposed in a first or proximal most position on the main handle 10 and the stent graft 42 at the proximal end 4 of the delivery device 2 is fully sheathed and held in a radially inwardly contracted condition as shown in FIGS. 1 and 13A. More specifically, with the stent graft 42 fully sheathed, the series of stents 50 on the main body of the stent 62 as well as the leg stents 72 are held in a radially inwardly contracted condition as shown in FIG. 13A, which is an enlarged view of a portion of the sheathed stent graft 42 in FIG. 13. As the second handle 12 is rotated to move it distally along the main handle 10, the protrusion 160 (such as a collar or ring on the inner surface 140 of the second handle 12) engages with a protrusion on the end cap 148 as shown in FIG. 10. As mentioned above, the second handle 12 can rotate freely and independently of the end cap 148. As the second handle 12 rotates and moves distally along the main handle 10, the end cap 148 is pushed distally, which in turn pushes the sheath connector 108 distally, thereby also pulling the sheath 104 distally, to expose a proximal end 44 of the stent graft 42, such as the top stent 46 and seal stent 56 portions of the stent graft as shown in FIGS. 15 and 16. Retracting the sheath 108 to expose a proximal end 44 of the stent graft 42, such as the top and seal stent 42, 56 may sometimes be referred to "exposing the diamond" by one of skill in the art. The longitudinal slot 134 formed in the main handle 10 accommodates the sheath flush port 116 on the sheath connector 108, such that as the second handle 12 is moved distally relative to the main handle 10, the sheath flush port 116 can slide distally along with the sheath connector 108 and the second handle 12 through this longitudinal slot 134 formed in the main handle 10.

By moving the second handle 12 distally relative to the main handle 10, a prosthesis release actuation mechanism 162, sometimes referred to herein as a "proximal suture drum 162" also becomes exposed and is now visible and accessible by the user as shown in FIG. 16. The proximal suture drum 162 is disposed about the main handle 10, just distal to the gripping portion 126 of the main handle 10 and just proximal to the nut 142. The proximal suture drum 162 is rotatable about the main handle 10. In other words, when the second handle 12 is disposed in a first or proximal most position on the main handle 10 as shown in FIGS. 12 and 14, the second handle 12 covers the proximal suture drum 162 so that the proximal suture drum 162 is not visible and cannot be accessed and/or manipulated (rotated) by the user. FIGS. 11 and 12 illustrate the second handle in a proximal most position on the main handle with a portion of the second handle 12 cut away to see the location of the proximal suture drum 162 hidden under the second handle 12. The proximal suture drum 162 may have one or more longitudinal grooves 164 on its outer surface (see FIGS. 12 and 18), which engage with one or more correspondingly shaped protrusions on the inner surface 140 of the second handle 12 to prevent premature or unintended rotation of the proximal suture drum 162 until the second handle 12 has been properly and sufficiently moved in a distal direction to expose the proximal suture drum 162. In other words, access to and rotation of the proximal suture drum 162 is prevented by the second handle 12 until an appropriate stage of a deployment sequence (i.e., after the second handle 12 has been retracted distally thereby withdrawing the sheath 104 a sufficient distance to expose at least the proximal end of the stent graft and deployment of the top stent 46 is appropriate and desired as described below). However, when the second handle is in the proximal most position on the main handle 10 as shown in FIG. 14, the prosthesis, such as a stent-graft 42 disposed on the delivery device 2 at a stent-graft retention region 16 is fully covered by the retractable sheath as shown in FIGS. 1 and 13.

Figure 17:
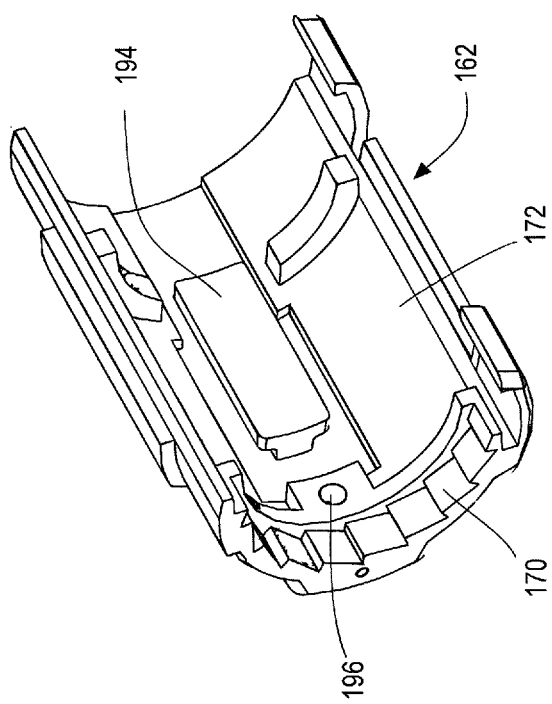
FIG. 17 is a cross sectional view of one example of a proximal suture drum.

As shown in FIG. 9, the main handle 10 may further comprise one or more radial protrusion(s) 168, such as a tooth or post. This protrusion 168 may be located just distal of the gripping portion 126 and is configured to engage with a ratchet 170 within the proximal suture drum 162 as shown in FIG. 17. In one example, the ratchet 170 within the proximal suture drum 162 may be integrally formed with at least a portion of an internal surface 172 of the proximal suture drum 162, or alternatively, the ratchet 170 may be a separate component that is connected or secured to the interior 172 of the proximal suture drum 162. Alternatively, in place of or in combination with the ratchet 170, a thin metal shim inserted within a radial slot formed in the wall of the inner surface 172 of the proximal suture drum 162 may serve as the ratchet that engages with the radial protrusion 168 extending from the outer surface 122 of the main handle 10.

Preferably, the ratchet 170 present on the inside 172 of the proximal suture drum 162 allows only for unidirectional rotation of the proximal suture drum 162. In other words, the ratchet 170 permits rotation of the proximal suture drum 162 in one particular direction, but prevents rotation of the proximal suture drum 162 in the opposite direction. For example, the ratchet 170 may be configured so that it engages with the radial protrusion 168 on the main handle 10 to prevent counterclockwise rotation of the proximal suture drum 162, but permits clockwise rotation of the proximal suture drum 162. It will be appreciated that the components of the handle assembly 8, including the proximal suture drum 162, may be designed to rotate in any particular direction, however, as described herein for exemplary purposes, the ratchet 170 is configured to permit clockwise rotation of the proximal suture drum 162 and prevent counter-clockwise rotation.

Figure 18:
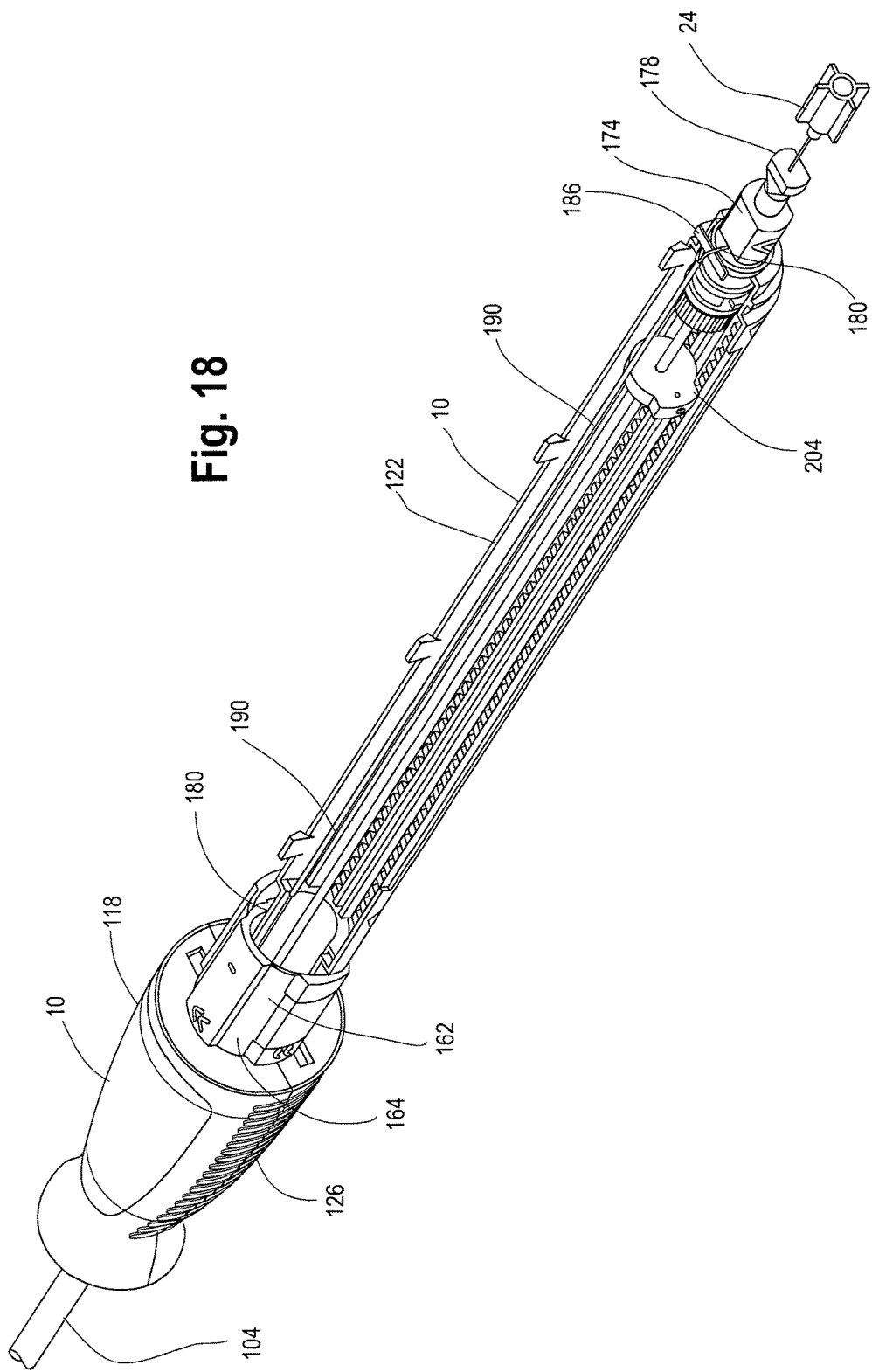
FIG. 18 is a partial sectional view of the interior of the handle assembly showing a suture extending between a proximal suture drum and a motion translating mechanism, or distal suture drum.
Figure 19:
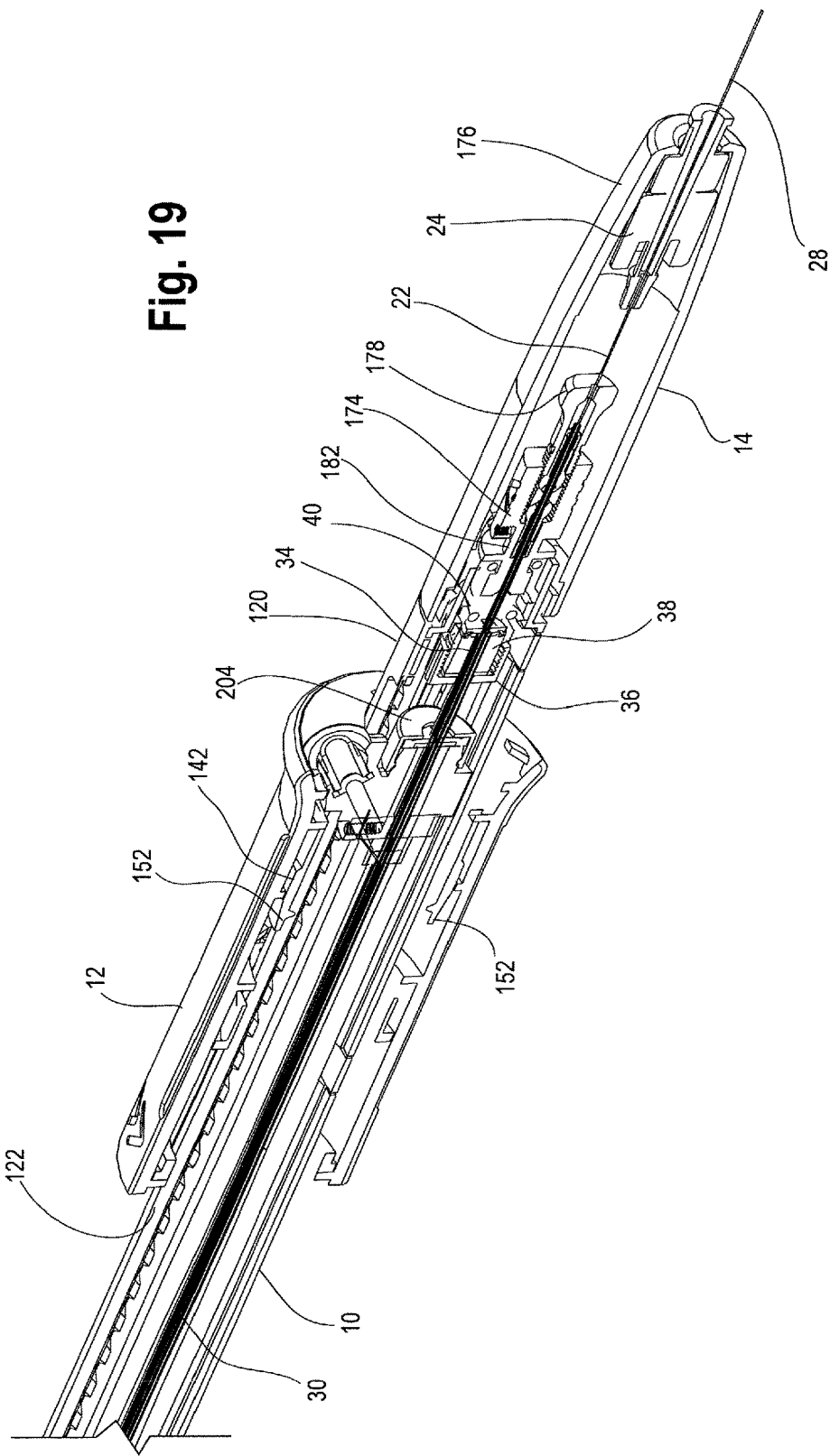
FIG. 19 is a cross sectional view of the distal end of the handle assembly showing the distal suture drum.

As depicted generally in FIGS. 16, 18 and 19, a motion translating mechanism 174, or distal suture drum 174, is disposed distal to the proximal drum 162 and is located within an end cap 14 at the distal end 120 of the main handle 10. The back end cap 14 may be a single structure or multiple parts or halves snap-fitted together and into engagement with the distal end 120 of the main handle 10. End cap 14 may have a distal taper 176 and may be removable or split open by the user should the need arise, such as in an emergency "bailout" procedure in the event that one or more components of the handle assembly 8 fail during deployment, thus allowing the user to remove the end cap 14 and access the handle interior 124, including the distal suture drum 174, to manually perform certain deployment steps described in further detail below. The inner cannula 22 extends distally through the back end cap 14 to the distal flush hub 24, as can be seen in FIG. 19.

With reference to FIG. 18, the distal suture drum 174 is operatively connected with the proximal suture drum 162. The distal suture drum 174 is disposed circumferentially around and connected to the inner cannula 22, such as by the pin vise 178, although other suitable mechanisms for attaching the inner cannula 22 to the distal suture drum 174 are also contemplated, including adhesives, for example. As will be discussed in greater detail below, the distal suture drum 174 is configured to rotate the inner cannula 22 to effect the release of the prosthesis 42 from the prosthesis retention mechanism 80.

Figure 20:
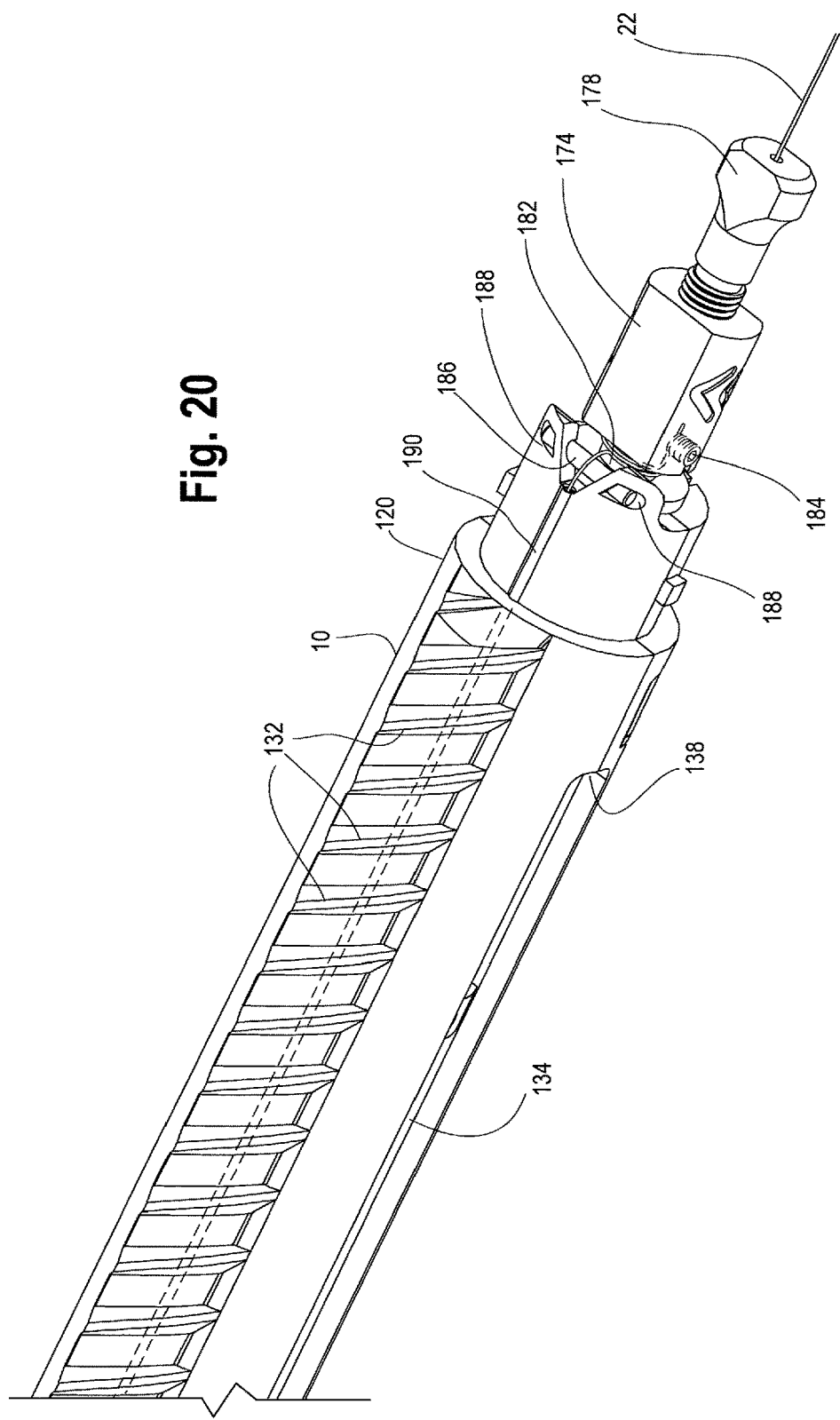
FIG. 20 is a perspective view of the distal end of the main handle and the distal suture drum.

In one non-limiting example, the proximal suture drum 162 (e.g. the prosthesis release actuation mechanism) is operatively connected to the distal suture drum 174 (e.g., the motion translating mechanism) by an elongated filamentous material 180, such as a suture, string, wire, cord, thread and the like. The suture 180 may be composed of ultra-high molecular weight polyethylene (UHMWPE); alternatively, a nitinol wire or other suitable materials may be utilized. The suture 180 serves to transfer motion of the proximal suture drum 162 to the distal suture drum 174. In one example, as shown in FIGS. 20 and 21, the suture 180 is pre-wound around the distal suture drum 174 at a suture-wrapping portion 182 a select number of times and secured to the distal drum 174, such as via a set screw 184 and/or a 4-40 screw thread. The suture 180 then extends from where it is wrapped around the suture wrapping portion 182 of the distal suture drum 174 over/around a pin 186 extending generally perpendicularly to the longitudinal axis of the main handle 10. In one example, each end of the pin 186 is held within an opening or slot 188 formed in the distal end 120 of the main handle 10. After wrapping up and over the pin 186, the suture 180 extends longitudinally forward or proximally through a small suture cannula 190 that is embedded in a sidewall of the main handle 10 or which extends longitudinally through the main handle 10 generally parallel to an inner surface 124 of the main handle 10. The suture 180 then exits the suture cannula 190 at a proximal location 192 on the main handle 10 adjacent to where the proximal suture drum 162 sits on the main handle 10, as shown in FIG. 22. The suture 180 exits the suture cannula 190 and is connected to the proximal suture drum 162. In one example, as FIG. 17 shows, the inner surface 172 of the proximal suture drum 162 has an attachment surface, such as a "J" peg and/or post 194 around which the suture 180 may be wrapped one or more times and then secured to the proximal suture drum 162 by a set screw 196. It is also contemplated that the suture 180 can be secured to the proximal suture drum 162 by other suitable attachment mechanisms, such as being threaded through an opening or aperture, tied, crimped and/or secured by adhesives or a combination thereof.

Figure 26:
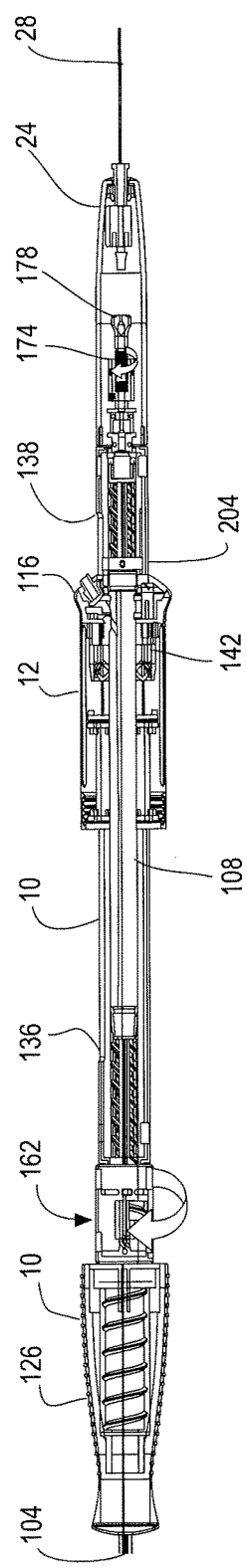
FIG. 26 is a side cross sectional view of the handle assembly of FIG. 23, showing rotation of the proximal suture drum effecting rotation of the distal suture drum and inner cannula to release a proximal stent.

When the proximal suture drum 162 is rotated (such as in a clockwise direction as indicated in FIG. 26) the suture 180 connected to the inner surface 172 of the proximal suture drum 162 starts to wind around a proximal portion 198 of the outer surface 122 of the main handle 10 as shown in FIGS. 9 and 22 (where the proximal suture drum 162 has been removed to show the detail and location of the suture 180 wrapping around proximal portion 198 of the main handle 10). The proximal portion 198 of the main handle 10 on which the suture 180 is wound may be smooth or bare, or alternatively, it may be threaded so that the suture 180 is wound in parallel loops so there is no overlap. Rotation of the proximal suture drum 162 by the user winds the suture 180 around the outer surface 122 of the main handle 10, and simultaneously, the suture 180 unwinds from the distal suture drum 174. In other words, as the proximal end of the suture 180 winds around proximal portion 198 of the main handle 10, the distal end of the suture 180 unwinds from the distal suture drum 174, thus causing the distal suture drum 174 to rotate. As the distal suture drum 174 rotates, the inner cannula 22 rotates along with it. Because the inner cannula 22 extends substantially the entire longitudinal length of the delivery device 2, the rotation of the distal suture drum 174 at the distal end 120 of the handle assembly 8 causes the inner cannula 22 to rotate along its entire length. Rotation of the inner cannula 22 along its entire length effects release of the prosthesis retention mechanism 80 from the proximal end 44 of the stent graft 42, such that the prosthesis retention mechanism moves from a prosthesis capture condition to a prosthesis release condition, as will be described below.

As shown in FIG. 22, the diameter 200 of the proximal suture wrapping portion 198 of the main handle on which the proximal suture drum 162 sits (and upon which the suture 180 becomes wrapped during use) may determine the diameter 202 (FIG. 21) of the distal suture wrapping portion 182 of the distal suture drum 174 upon which the suture 180 is wrapped. For example, it may be preferable that a user grips and/or re-grips a rotating part, such as the proximal suture drum, three times to enable one complete 360 degree rotation of the proximal suture drum 162. Thus, it may be desirable for the user to rotate the proximal suture drum 162 one or 1.5 times to effect release of a proximal end (i.e., the top stent 46) of the prosthesis 42. At the same time, in order for the proximal stent apices 66 (and/or apertures or loops 74 on the top stent 46) to be uncoupled from the coiled member 84 on the inner cannula 22, the cannula 22 needs to rotate approximately 3-4 times (i.e., 3-4 complete revolutions if considering tortuous anatomy) to safely release the top stent 46. In other words, one complete rotation of the proximal suture drum 162 preferably causes 3-4 rotations of the distal suture drum 174, which may be accomplished by making the distal suture drum diameter 202 upon which the suture 180 wraps approximately 3-4 times smaller than the diameter 200 of the proximal suture wrapping portion 198. This may be calculated using the following exemplary equation:

$$\varphi(\text{Diameter of distal suture drum upon which the suture is wrapped}) = \frac{\varphi\left(\begin{array}{c}\text{Diameter of outer surface of}\\\text{main handle upon which the suture wraps}\end{array}\right)}{n}$$

where $n$ = number of rotations of the inner cannula required to deploy the top stent.

Thus, in one non limiting example, $$n = 3 \text{ or } 4 \text{ rotations of the inner cannula.}$$

It should be understood that this configuration of the present invention is not limiting and that one skilled in the art would appreciate that different diameters of the proximal and distal suture drums 162, 174 can be used to achieve a desired number of rotations of the inner cannula 22 to effect the release of a prosthesis 42.

With the sheath 104 retracted to expose the top stent 46 and/or seal stents 56 at the proximal end 44 of the stent graft 42 and the proximal suture drum 162 visible and accessible, as shown in FIGS. 15 and 16, the user may continue to rotate the second handle 12 to further move the second handle 12 distally along the main handle 10 to further retract the sheath 104 and expose the main body 62 of the stent graft 42 and, depending on the length of the contralateral limb 58, also expose at least a portion of the contralateral limb 58 as shown in FIG. 23 and FIG. 24. In cases where the contralateral limb 58 is relatively short, the second handle 12 may only need to be moved distally on the main handle 10 to a position such as that shown in FIG. 23 and the contralateral limb 58 may be fully exposed. On the other hand, in cases where the contralateral limb 58 is relatively longer, the second handle 12 must be moved distally on the main handle 10 as far back as the distal trigger wire knob 204 in order to fully un-sheath and expose the contralateral limb 58 as shown in FIG. 26.

The second handle 12 may continue to move distally until the distal end 14 of the sheath connector 108 within the second handle 12 and/or the end cap 148 touches, meets, abuts or is otherwise adjacent to a distal trigger wire knob 204 located within the main handle interior 124, as shown in FIGS. 26 and 28. The user may feel a slight resistance which signals that the sheath connector 108 has reached the distal trigger wire knob 204. Other visual or mechanical signals may also be present on the delivery device 2 and/or handle assembly 8 to indicate to the user to stop rotating the second handle 12 (to thereby stop further distal movement of the second handle 12 along the main handle 10) including visual cues provided by desired imaging modality (i.e., by fluoroscopy, MRI, 3D or other imaging techniques). At this point, distal movement of the second handle 12 relative to the main handle 10 has moved the sheath connector 108 distally, thereby retracting the sheath 104 a sufficient travel distance 206 such that the top stent 46, stent-graft main body 62 and at least a portion of the contralateral limb 58 has been exposed. The ipsilateral limb 60, however, is still sheathed, as shown in FIG. 24.

At this stage, the top stent 46 may be released as shown in FIG. 25 by rotating the proximal suture drum 162 as shown in FIG. 26. As previously mentioned, release of the top stent 46 may be accomplished by clockwise rotation of the proximal suture drum 162. Rotation of the proximal suture drum 162, which is operatively connected to the distal suture drum 174 via the suture 180, thereby effects rotation of the inner cannula 22 (including the prosthesis retention mechanism 80 at the proximal end of the cannula 22) to enable release of the top stent apices 66 or loops 74 captured by the coil or helix 84, as shown in FIGS. 4 and 5.

As previously mentioned, the components of the handle assembly 8, including the proximal suture drum 162, distal suture drum 174 and/or inner cannula 22 (including the prosthesis retention mechanism 80 or coiled member 84) may be designed, manufactured and assembled to rotate in any particular direction (clockwise and/or counterclockwise). Any particular direction as described and designated herein is for exemplary purposes only and should not be considered so limiting. In one example, the proximal suture drum 162 may be rotated clockwise, but the direction that the distal suture drum 174 rotates may depend on how the suture 180 is pre-wound on the distal suture drum 174 (either clockwise wound or counter-clockwise wound). Thus, rotation of the proximal suture drum 162 (i.e., the prosthesis release actuation mechanism) in a first direction effects rotation of the distal suture drum 174 (i.e., the motion translating mechanism) in a second direction and wherein rotation of the distal suture drum 174 (i.e., the motion translating mechanism) effects rotation of the inner cannula 22 and the coiled member 84 (i.e., the prosthesis retention mechanism 80) in a third direction. The first, second and third directions may be the same, or the first, second and third directions may be different, or a combination thereof. In a non-limiting example, the proximal suture drum 162 may be rotated clockwise by the user, and the suture pre-wrapped upon the distal suture drum 174 in a clockwise direction, which, when unwound from the distal suture drum 174, rotates the distal suture drum 174 in a clockwise direction thereby rotating the inner cannula 22 in a clockwise direction. Alternatively, the proximal suture drum 162 may be designed and assembled for counterclockwise rotation, as can the distal suture drum 174 and/or inner cannula 22.

After the top or proximal stent 46 has been released, the second handle 12 can then be moved further distally relative to the main handle 10 (from the position shown in FIGS. 23, 26 and 28) to a final or distal most position on the main handle 10 (as shown in FIG. 29) to further retract the sheath 104 while simultaneously withdrawing one or more distal trigger wires to thereby deploy the ipsilateral limb 60 of the stent graft 42 as shown in FIG. 27. This final distal movement of the second handle 12 to a position on the main handle 10 (as shown in FIG. 29) may be accomplished by the user continuing to rotate the second handle 12 relative to the main handle 10 as described above, where rotation of the second handle 12 causes the second handle 12 to travel distally in a longitudinal direction along the main handle 10. Alternatively, rather than continuing to rotate the second handle 12 to move it distally, the user has the option to implement a "quick release" protocol in order to retract the second handle 12 distally without rotation, as will be described in further detail below.

Figure 30:
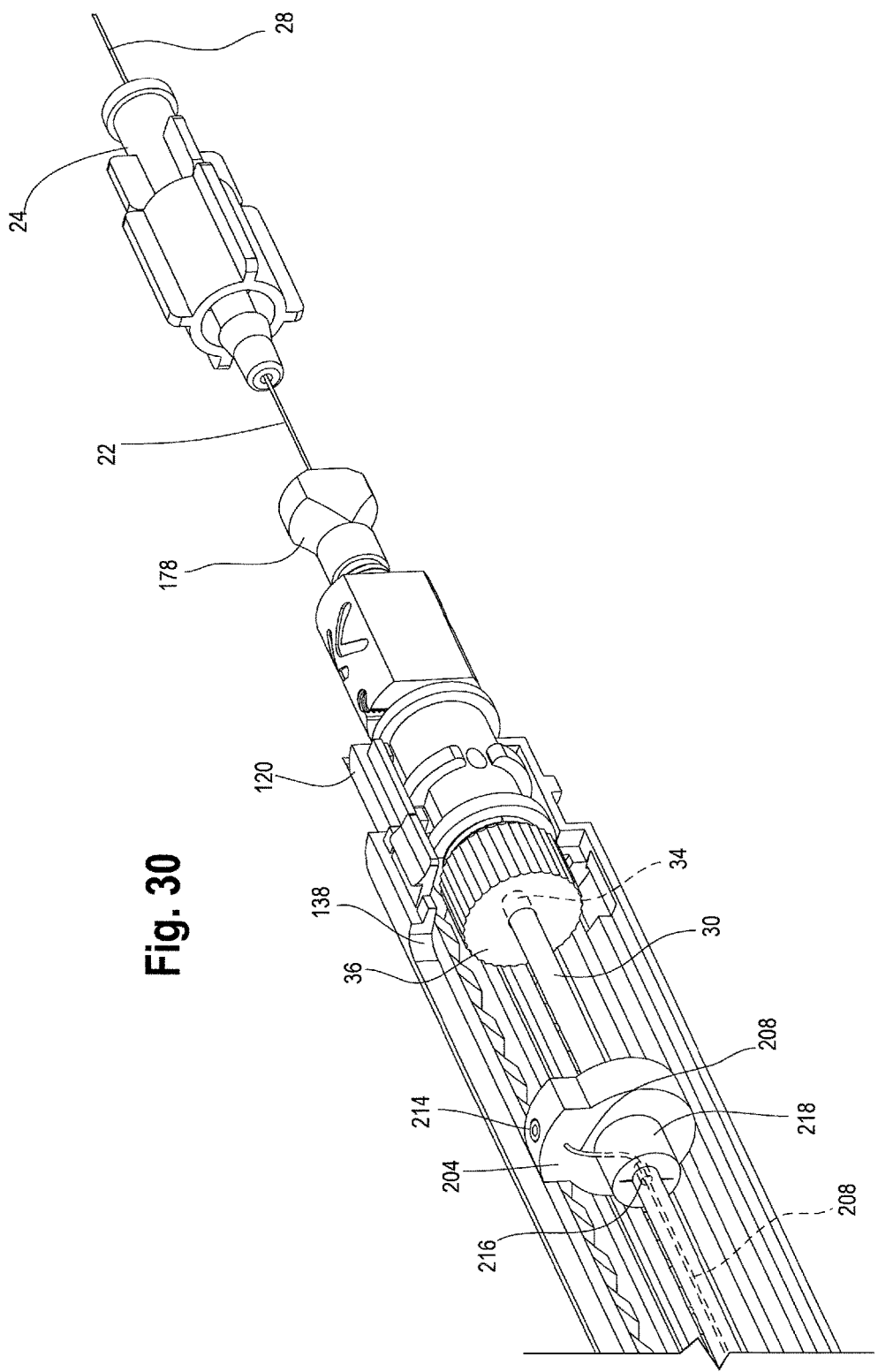
FIG. 30 is a cross sectional view of the distal end of one example of the handle assembly showing the distal trigger wire knob, distal suture drum and a distal flush hub.

The distance of travel of the second handle 12 relative to the main handle 10 to this final or distal most position is identified as reference number 210 in FIG. 29. In other words, distal movement of the second handle 12 from a second or an intermediate position in FIG. 28 to the distal most position in FIG. 29 causes the sheath connector 108 to retract distally (thereby retracting the sheath 104 distally) to expose the ipsilateral limb 60 of the stent graft 42. At the same time, the distal end of the second handle 12 and/or the distal end 114 of the sheath connector pushes against a distal trigger wire release mechanism 204 located within the main handle 10. As shown in FIG. 30, the distal trigger wire release mechanism 204 is a ring that is slidably disposed over the positioner 30. One or more distal trigger wire(s) 208 extend proximally from the distal trigger wire release mechanism 204 to the distal end of the stent-graft 48.

In one example, the positioner 30 provides a conduit for the distal trigger wires 208 to extend from the trigger wire release mechanism 204 in the main handle 10 to the distal end 48 of the stent graft 42. As shown in FIG. 30, one or more trigger wires 208 may be secured to the distal trigger wire release mechanism 204 by a set screw 214. The trigger wire 208 then extends from the trigger wire release mechanism 204 and into an opening, hole or aperture 216 formed in the positioner 30, where the distal trigger wire(s) 208 further extend proximally through the conduit provided by the positioner 30 to the distal end 48 of the stent graft 42. A seal 218, such as a silicone sleeve or disc may be provided to cover the hole 216 formed in the positioner 30 and prevent back-leakage of fluids through the hole 216.

The distal trigger wire(s) 208 may be directly or indirectly attached to the distal end 48 of the stent graft 42. For example, the distal trigger wires 208 may engage a suture (not shown) which is attached to the distal end 48 of the ipsilateral limb 60 of the stent-graft 42. Alternatively, the distal trigger wire 208 may be woven directly through or removably attached to the graft material 52 or one or more stents 72 at the distal end of the graft 42. Other suitable attachment methods or mechanisms may be used to removably attach the distal trigger wires 208 to the distal end of the stent graft 42 as would be recognized by one of skill in the art.

As FIGS. 27-29 illustrate, distal movement of the second handle 12 pushes or drives the distal trigger wire knob 204 distally with it, thereby pulling the one or more distal trigger wires 208 in a distal direction. The proximal end of the distal trigger wire(s) 208 thereby are withdrawn or become disengaged from the distal end of the stent graft 42 (i.e., the distal trigger wires 208 become released from the suture loop and/or become disengaged from the graft material 52 at the distal end of the ipsilateral limb 60). Distal movement of the second handle 12 ceases upon second handle 12 reaching the distal end 138 of the longitudinal slot 134 formed in the main handle 10 and/or when the distal trigger wire knob 204 abuts or contacts the stationary collar 36 at the distal end 120 of the main handle 10.

Turning now to FIGS. 23-29, the steps of a "quick release" procedure are described. As set forth above, second handle 12 can rotate about the longitudinal axis of the main handle 10 to move the second handle 12 distally, thus retracting the sheath 104 to expose the proximal stent 46, the main body 62 and the contralateral limb 58 of the stent graft 42 as shown in FIG. 24. The threaded engagement between the inner surface 152 of the nut 142 and outer surface 122 of the main handle 10 necessitates rotation to impart longitudinal movement of the second handle 12 relative to the main handle 10. The user may continue to rotate the second handle 12 to move it distally to further retract the sheath 104 to expose the ipsilateral limb 60 and release the trigger wires 208 from the distal end of the stent graft 42 during deployment. However, as an alternative, the "quick release" procedure may now be employed at this stage of deployment, if desired, in order to further retract the sheath 104 to expose the ipsilateral limb 60 and to release the distal trigger wires 208 without having to rotate the second handle 12 relative to the main handle 10.

More specifically, instead of rotating the second handle 12, the "quick release" procedure provides the user the ability to slide the second handle 12 freely longitudinally along the main handle 10 without rotation in a straight pull-back motion, so that the second handle 12 can simply slide longitudinally along the main handle 10 in a continuous smooth non-rotating motion. This provides several advantages, including, for example, the user being able to retract the second handle 12 more quickly and without rotation to complete sheath retraction and distal trigger wire removal. It also facilitates a final stage of a procedure once the entire stent graft 42 is deployed, allowing the user to re-sheath or recapture at least a portion of the nose cone 18 of the delivery device 2 within the sheath 104 for removal of the device 2 from a patient's body as will be described in further detail below.

In the first steps of the "quick release" procedure, the user can firmly grip the gripping portion 126 of the main handle 10 with one hand while pulling back on an outer ring 220 located on the second handle 12 with the other hand as FIG. 28 shows to "release" or disengage the second handle 12 from the main handle 10, thus allowing the second handle 12 to slide freely longitudinally along the main handle 10 without rotation in a straight pull-back motion.

More specifically, as shown in FIGS. 31 and 32, the nut 142 located within the second handle 12 extends at least partially circumferentially around at least a portion of the main handle 10. As shown in one example in FIG. 31, the inner surface of the nut 142 is engaged with threads 132 on the outer surface 122 of the main handle 10 by a threaded engagement, although other mechanisms may be used to provide engagement between the nut 142 and the main handle 10. With the inner surface 152 of the nut 142 engaged with the outer surface 122 of the main handle 10, the second handle 12 must be rotated in order to move the second handle 12 distally along the main handle 10 (such as during the previously-described steps of moving the second handle 12 distally to facilitate sheath retraction and proximal stent deployment.)

As shown in FIGS. 31 and 32, a sleeve 222 extends at least partially circumferentially over and/or around the nut 142, or alternatively, the sleeve 222 may completely surround or enclose a portion of the outer surface of the nut 142. In one non-limiting example, the sleeve 222 may be a curved, arcuate and/or semi-circular structure that is positioned on the outer surface of the nut 142, as shown in FIG. 31 A. The outer surface of the sleeve 222 may have one or more radially outwardly extending protrusions 224 that extend through one or more openings or slots 226 formed in the second handle 12 (see FIG. 10) so as to engage with an opening or channel formed in the inner surface of the ring 220. Any other suitable mechanisms and/or correspondingly shaped structures on the sleeve 222 that are configured to allow the sleeve 222 to connect to or operatively engage with the ring 220 may also be used as would be recognized by one of skill in the art.

When the ring 220 is in a first or proximal position relative to the second handle 12 as shown in FIG. 31, the sleeve 222, which is operatively engaged with the ring 220 as previously described, is also positioned at a proximal end of the nut 150. The sleeve 222 holds the proximal end 150 of the nut 142 in a radially inwardly compressed condition and prevents such outward flaring of the nut 142. Thus, the sleeve 222 maintains and/or urges the nut 142 radially inwardly and the urges the threads on the inner surface 152 of the nut 142 into engagement with the outer surface 122 of the main handle 10. Thus, when the ring 220 is in this first or proximal position on the second handle 12 (FIG. 31), the nut 142 is engaged with the main handle 10 such that the second handle 12 must be rotated to move the second handle 12 longitudinally in a distal direction.

However, during quick release, the ring 220 is moved from the first proximal position to a second distal position (shown in FIG. 32) by the user to move the sleeve 222 distally relative to the nut 142. As shown in FIG. 32, when the sleeve 222 is moved distally, the proximal end 150 of the nut 142 is permitted to expand radially outwardly so that the inner surface 152 of the nut 142 is released from engagement with the main handle 10. In one example, the nut 142 is self expanding, such that when the sleeve 222 is moved distally, the proximal end 150 of the nut 142 may expand radially outwardly without the aid or assistance of mechanical expansion techniques because the proximal end 150 of the nut 142 may have a tendency to flare radially outwardly in a natural or relaxed position. However, in another example, the nut 142 may also be mechanically expanded. In particular, as shown in FIG. 31A, the proximal portion 228 of the sleeve 222 includes an expanding structure 230 that is configured to engage with at least a portion of the inner surface 152 of the nut 142 and urge the proximal end 150 of the nut 142 radially outwardly. Thus, as the sleeve 222 is moved distally, the expanding structure 230 comes into contact with the proximal end 150 of the nut 142 to radially outwardly expand the proximal end 150 of the nut 142. The inner surface 152 of the nut 142 thus becomes disengaged from the main handle 10 allowing the second handle 12 to be moved distally along the main handle 10 without rotation.

The expanding structure 230 may be in the form of a ring, partial ring, semi-circle, wedge and/or any other structure that facilitates radial expansion of the nut 142. As shown in FIGS. 31, 31 A and 32, the expanding structure 230 is a semi-circular structure that is located just proximal to and connected to the sleeve 222. The expanding structure 230 has a radius that is smaller than the radius of the sleeve 222. When the ring 220 is pulled distally back, the sleeve 222 with the expanding structure 230 also moves distally back. The expanding structure 230 drives itself between the outer surface 122 of the main handle 10 and the inner surface 152 of the proximal end 150 of the nut 142, thus urging the proximal end 150 of the nut 142 in a radially outwardly expanded condition. Thus, even if the nut 142 is self expanding but somehow fails to self-expand upon movement of the ring 220 (and simultaneously, the sleeve 222) to a distal position, then the expanding structure 230 will facilitate the radially outward expansion of the proximal end 150 of the nut 142 to disengage the nut 142 from the main handle 10, allowing the quick release procedure to still be utilized. A self-expanding nut 142 may fail to sufficiently expand or become deformed so that it cannot fully disengage from the main handle 10 because of age and/or sterilization, for example. Alternatively, if the nut 142 is not self-expanding and is dependent on mechanical expansion, the expanding structure 230 serves to facilitate the radially outward expansion of the proximal end 150 of the nut 142 during the quick release procedure.

In a non-limiting example, the action of sliding outer ring 220 distally may also make visible an arrow (or set of arrows or other similar markings) on the second handle 12 which serve as an indicator to the user that the second handle 12 is ready for "quick release" by straight distal pull-back of the second handle relative to the main handle 10. At this time, with the proximal end 150 of the nut 142 flared radially outwardly as shown in FIG. 32, the second handle 12 is disengaged from the main handle 10 and can be slid distally towards the user (without rotation) so that further retraction of the sheath 104 to expose the ipsilateral limb 60 can be completed while simultaneously withdrawing the distal trigger wire(s) 208 to fully release the stent graft in the vasculature as shown in FIG. 27, thus accomplishing a "quick release" portion of the procedure.

Another embodiment of the handle assembly 8 is shown in FIGS. 33-38, where like reference numbers identify like features as previously described, where appropriate. As shown in FIGS. 33-38, the handle assembly 8 further comprises a notched or threaded rack-like mechanism 232 which engages with the proximal suture drum 234. In a non-limiting example, the rack 232 has a proximal end 236 and a distal end 238, and has threads 240 formed on at least a portion of the rack's outer surface extending between the proximal and distal ends 238. The rack 232 is located inside the main handle 10 near the proximal end of the main handle 10. A slot or channel 242 formed in the proximal end 118 of the main handle 10 allows the rack 232 to travel longitudinally in a proximal direction inside the main handle 10.

Figure 35:
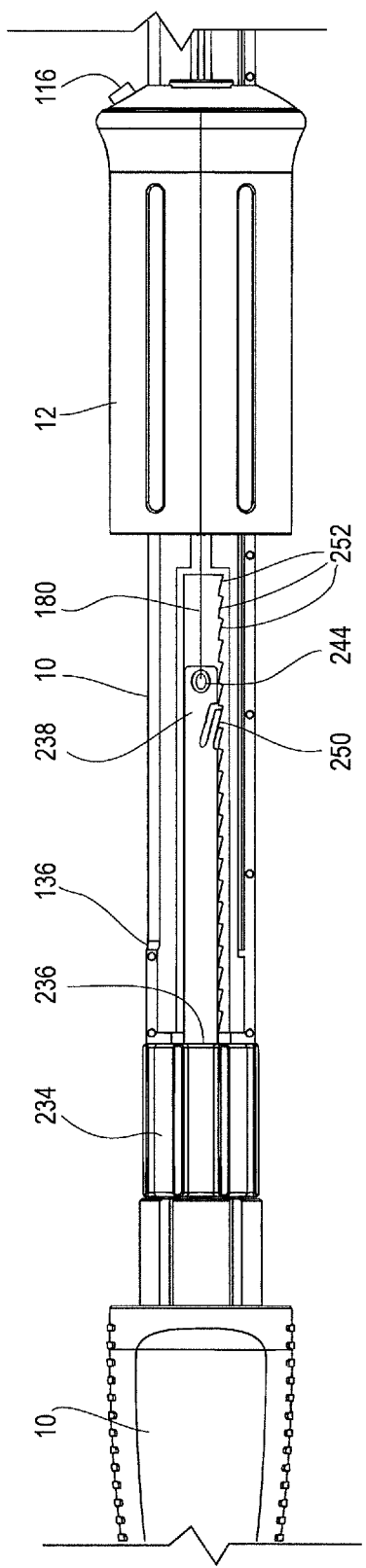
FIG. 35 is a side view of the handle assembly of FIG. 33 showing the rack within the main handle.
Figure 36:
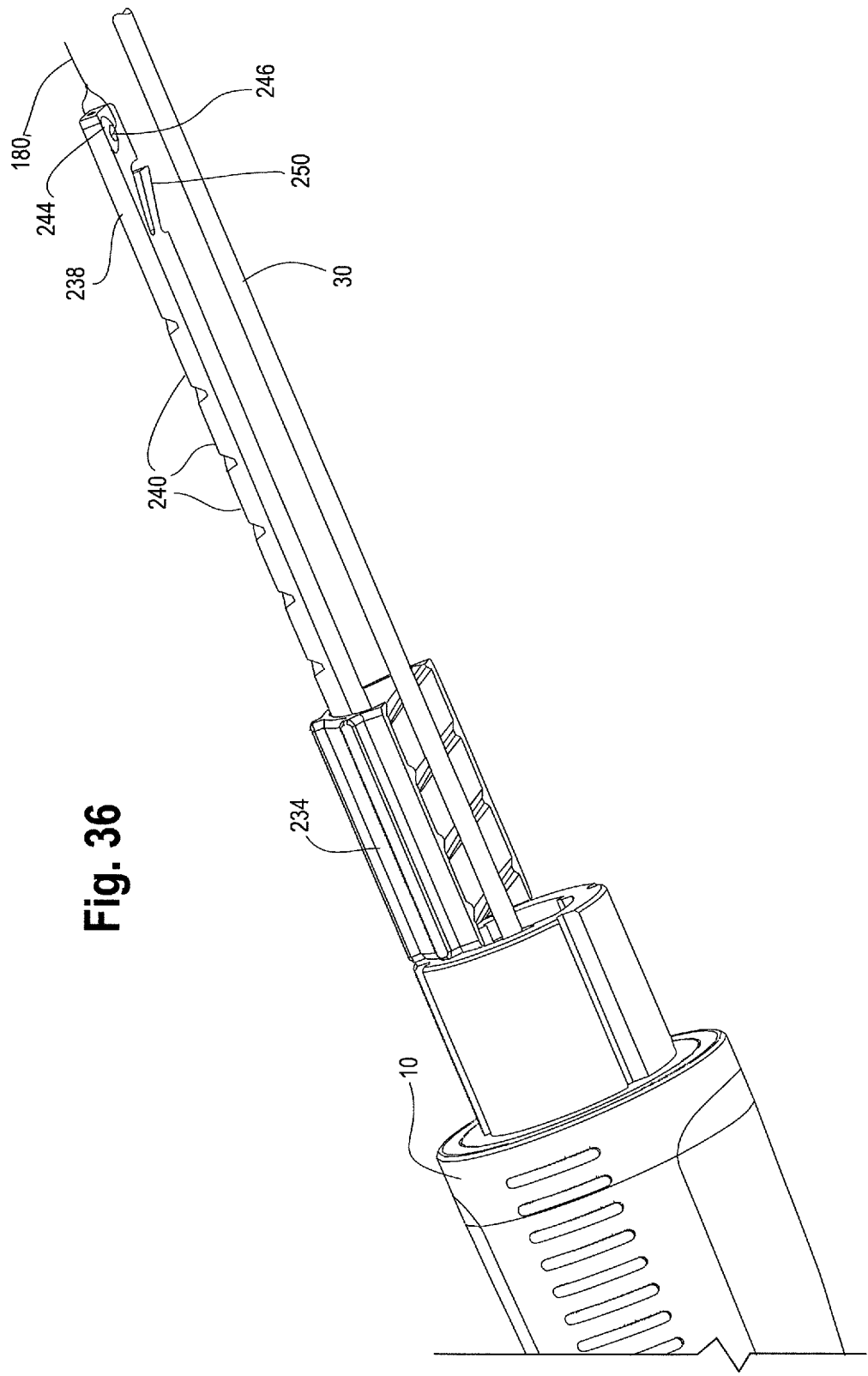
FIG. 36 is an enlarged perspective view of the rack within the main handle of FIG. 33.
Figure 37:
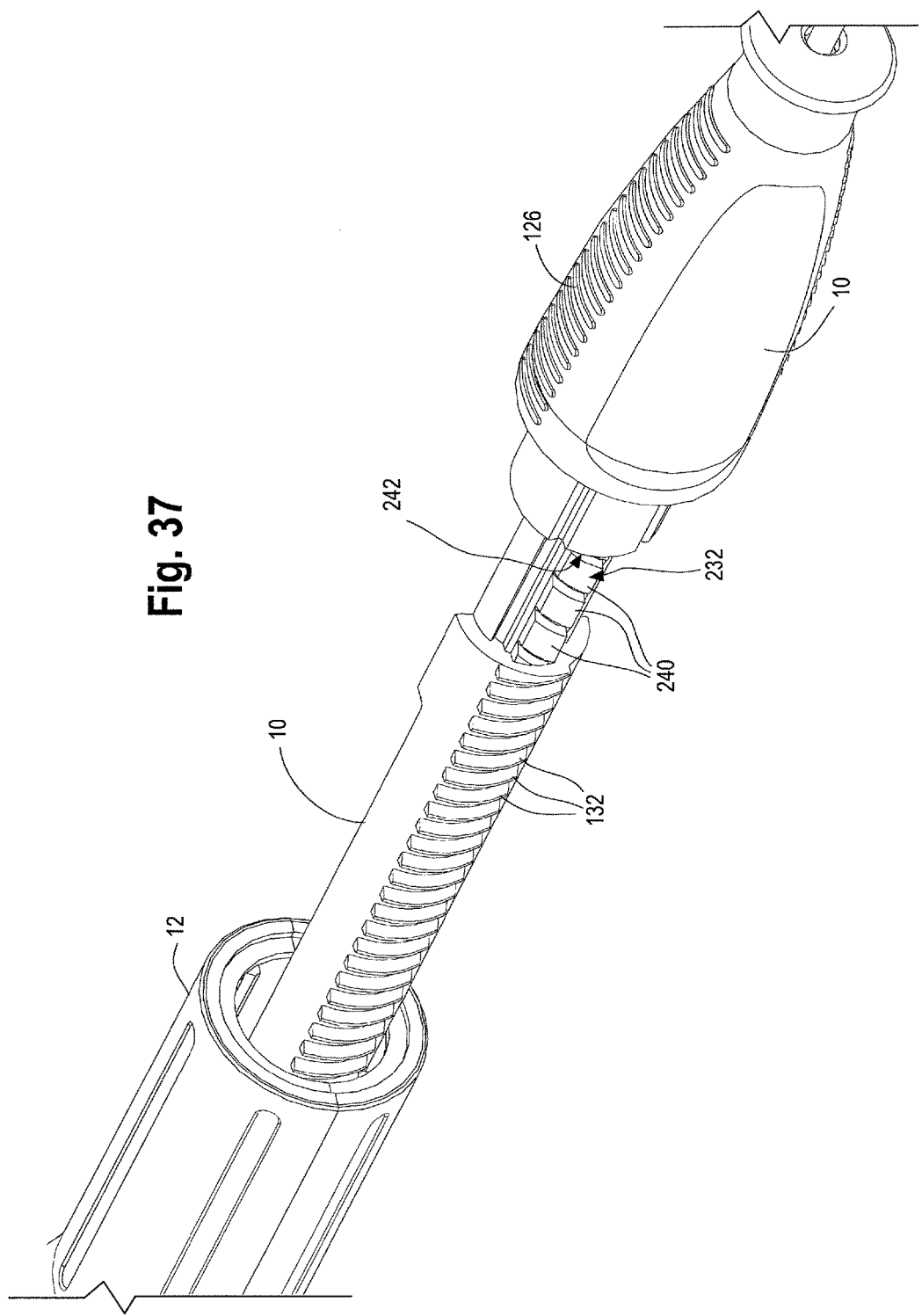
FIG. 37 is an enlarged perspective view of the rack within the main handle of FIG. 36.

The proximal end of the suture 180 is secured to or otherwise connected to the rack 232 as shown in FIGS. 35 and 36. For example, the suture 180 may be secured to the distal end 238 of the rack 232 via a J post or set screw 246, or alternatively or in combination, the suture 180 may be threaded or tied around or through an aperture or slot 244 formed in the distal end 238 of the rack 232 and/or secured to the rack with adhesives or other suitable attachment mechanisms. The threads 240 on the outer surface of the rack 232 are engageable with threads 248 formed on the inner surface of a proximal suture drum 234, shown in FIG. 38.

When the proximal suture drum 234 is rotated, threads 248 on the inner surface of the proximal suture drum 234 engage with the threads 248 on the rack 232, thus pulling or moving the rack 232 longitudinally in a proximal direction. As the rack 232 moves longitudinally in a proximal direction, the rack 232 thereby pulls the suture 180 proximally along with it, thus pulling the suture 180 off the distal suture drum 174. As the suture 180 is pulled off the distal suture drum 174, the distal suture drum 174 rotates, and in turn, rotates the inner cannula 22 along its entire length. In the same manner as already described in detail above, rotation of the inner cannula 22 causes the prosthesis retention mechanism 80 to release the prosthesis 42 carried at the proximal end 4 of the delivery device 2.

Figure 33:
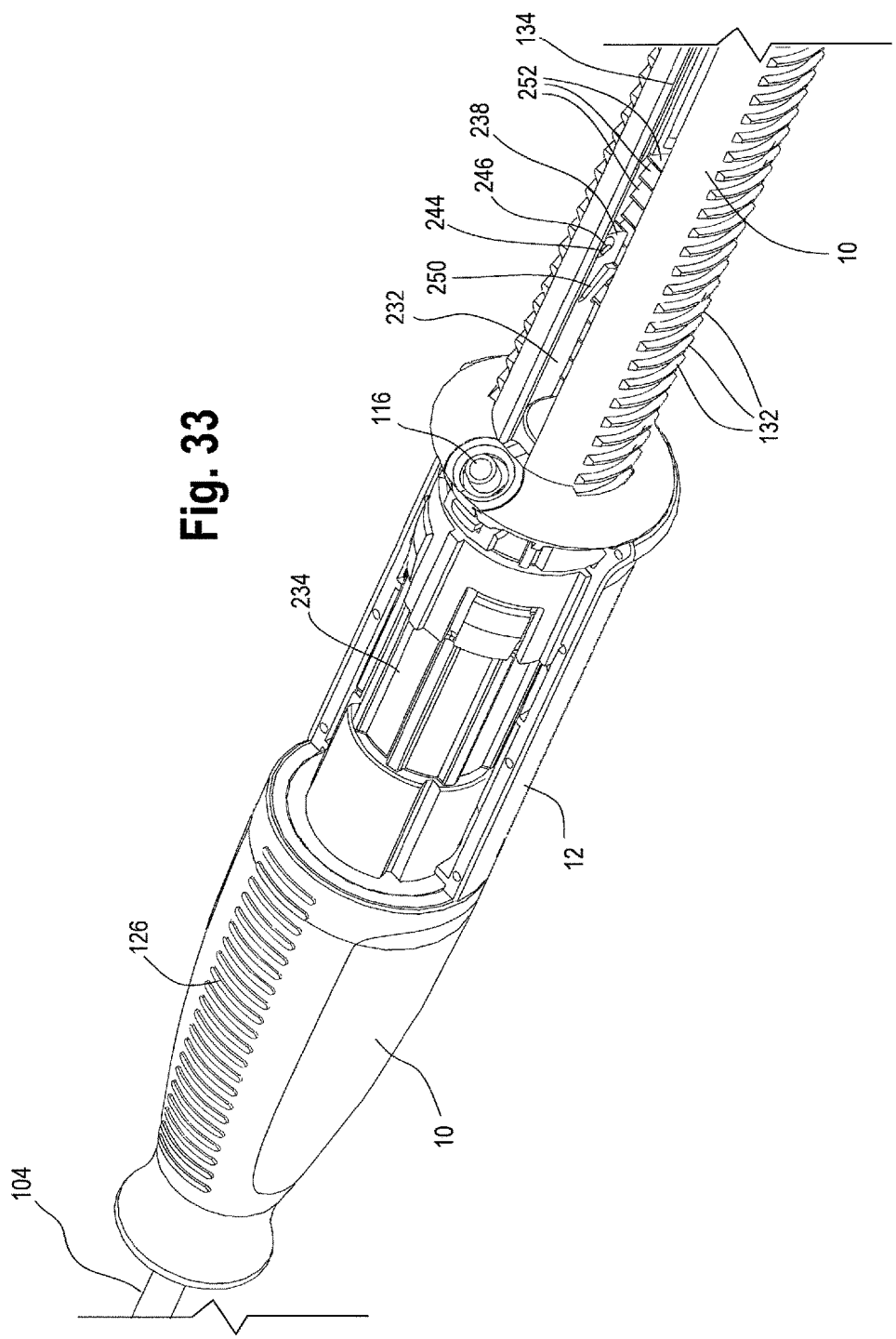
FIG. 33 is a perspective view of another example of the handle assembly including a rack, with a portion of the second handle removed to show another example of a proximal suture drum.
Figure 34:
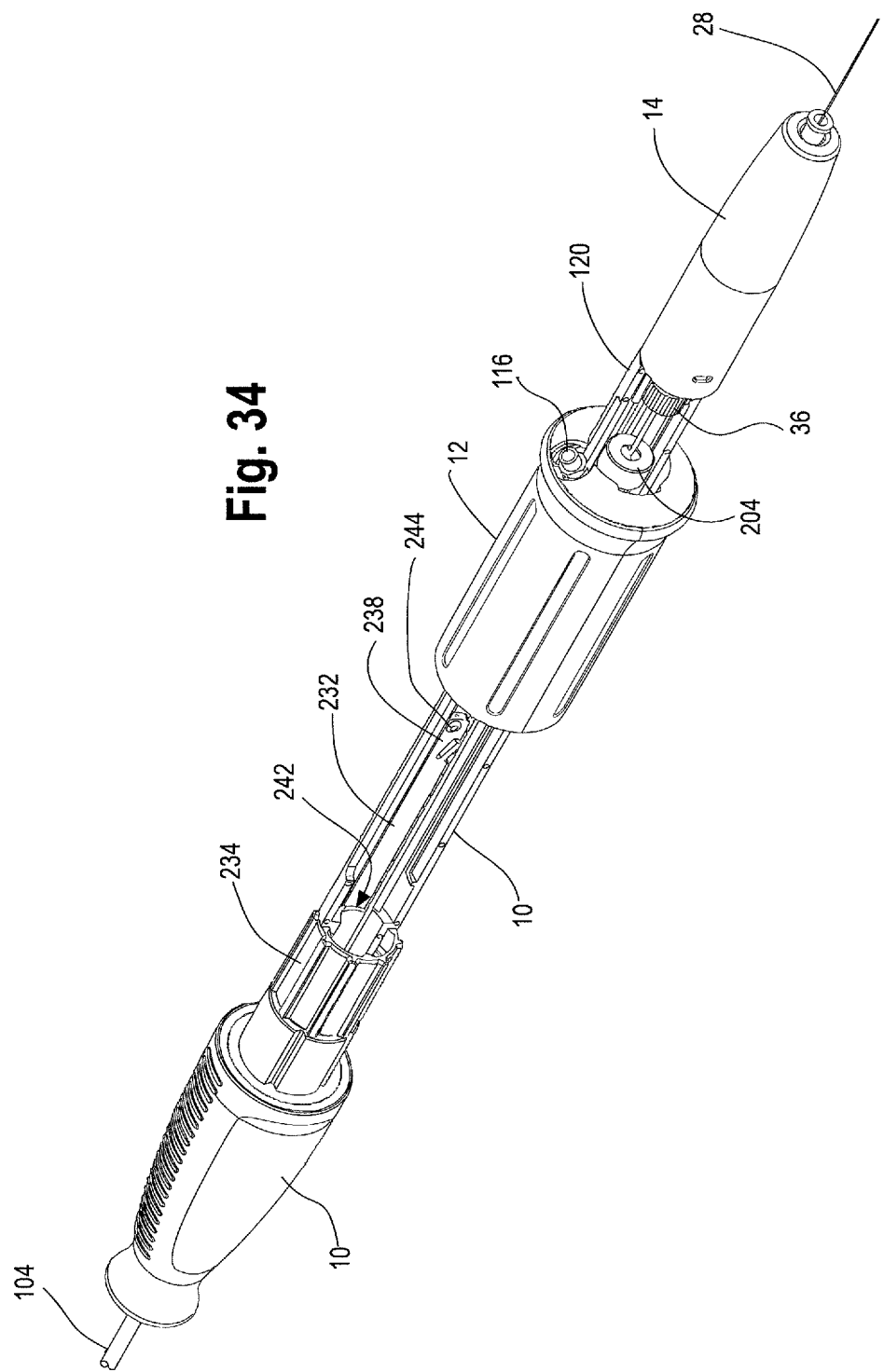
FIG. 34 is a perspective view of the handle assembly of FIG. 33 showing the second handle moved distally relative to the main handle, thereby exposing the proximal suture drum.

As shown in FIGS. 35 and 36, the rack 232 may further include one or more protrusions, fingers or teeth. For example, there may be several finger-like protrusions 250 disposed on an upper and/or lower surface of the rack 232. The protrusions 250 may be angled relative to a central or longitudinal axis of the rack 232 as shown in FIG. 35. A portion of the inner surface 124 of the main handle 10 may comprise one or more correspondingly shaped and/or angled protrusions or teeth 252 as shown in FIGS. 33 and 35. The angle of the teeth 252 on the inner surface of the main handle 10 are such that they permit the rack 232 to move proximally forward within the main handle 10 as the user rotates the proximal suture drum 234, however, the angle and/or shape of the teeth 252 on the inner surface of the handle do not permit the rack 232 to move distally backwards within the main handle 10. Thus, for example, the user may grip the proximal suture drum 234 and begin to rotate the proximal suture drum 234, thus pulling the rack 232 proximally within the main handle 10 and causing the suture to unwind from the distal suture drum 174. Then, if the user were to release or loosen the grip on the proximal suture drum 234, the rack 232 would not automatically revert or slide back or distally within the main handle 10 to its initial position which may be present due to, for example, tension in the distal suture drum 174 tending to pull the suture 180 (as well as the rack 232) backwards or distally. In other words, the engagement between the protrusions 250 on the rack 232 and the teeth 252 on the inner surface of the main handle 10 will serve to maintain the proximal travel progress of the rack 232, and will not allow the rack 232 to slide or drift distally back within the main handle 10.

Maintaining the proximal travel progress of the rack 232 thereby also maintains the number of rotations achieved by the distal suture drum 174 as well as the number or rotations of the inner cannula 22. Thus, the user can be confident that the number of rotations accomplished by the inner cannula 22 to release the prosthesis retention mechanism (coil 84) at the proximal end 4 of the device 2 cannot unknowingly or unwittingly become "undone" because the rack 232 and suture 180 cannot revert or travel distally backwards within the main handle 10 to thereby rotate the distal suture drum 174 and inner cannula 22 in an unwanted reverse direction and possibly tangle the coil 84 with the proximal apices 66 or loops 74 of the stent graft 42.

To illustrate several non-limiting differences between the "rack" embodiment of the handle assembly 8 and the first embodiment described herein, it can be seen that in the handle assembly 8 comprising the rack 232, the suture 180 is not directly attached to the proximal suture drum 234, therefore, rotation of the proximal suture drum 234 by the user does not cause the suture 180 to wrap around an outer surface 198 of the main handle 10 as in the previously described embodiment (see FIGS. 17 and 22, where the suture 180 is attached to the proximal suture drum 162 for wrapping the suture 180 around the main handle 10 at portion 198). Instead, with the addition of a rack 232 to the handle assembly 8 as described herein, the proximal suture drum 162 engages directly with the rack 232. As such, the proximal suture drum 162 includes threads 248 on its internal surface, such that rotation of the proximal suture drum 162 by the user engages threads 240 on the rack 232 thereby pulling or urging the rack 232 forward or proximally, thereby pulling the suture 180 proximally (because the suture 180 is connected to the distal end 238 of the rack 232). However, proximal movement of the suture 180 due to rotation of the proximal suture drum 234 and unwinding of the suture 180 from the distal suture drum 174 to impart rotation to the distal suture drum 174 and to the inner cannula 22 to effect release of the prosthesis retention mechanism 80 remains substantially the same.

The operation of the delivery device 2, and in particular the handle assembly 8 of the delivery device 2, will be described. In this example, use of the delivery device 2 will be described in reference to the implantation of a stent-graft 42, such as the one shown in FIG. 3 in an aorta 254 of a patient. After an incision is made in the femoral artery of the patient, the nose cone dilator 18 is inserted into the incision and the device 2 is tracked over a guide wire 28 and advanced through the artery to the desired location, for example the abdominal aorta 254 for placement of the stent-graft 42 at the site of an aneurysm, with the atraumatic tip 20 of the nose cone dilator 18 reducing the likelihood of injury to bodily passageways. The outer sheath 104 is disposed over the stent-graft 42 during insertion and delivery to the target site, as shown in FIGS. 1 and 13. A mechanism such as the pin vise 178 may be used to prevent longitudinal/axial movement of the inner cannula 22 during delivery to target location.

Upon proper positioning at the target site using a desired imaging modality (i.e., by fluoroscopy, MRI, 3D or other imaging techniques) the user grasps the gripping portion 126 of the main handle 10 with one hand, and using the other hand, grasps the second handle 12. The second handle 12 may be rotated relative to the main handle 10 to move the second handle 12 distally along the main handle 10, thereby retracting the sheath 104 to expose at least a proximal portion of the stent-graft 42. For example, the user may retract the sheath 104 to expose the top and/or seal stents 46, 56, sometimes referred to as the exposing the "diamond" at this stage of deployment as shown in FIG. 15. At this stage, the second handle 12 has been moved distally a sufficient distance such that the proximal suture drum 162 is also accessible and visible to the user (see FIG. 16). The user may continue to move the second handle 12 distally (such as by rotating the second handle 12 relative to the main handle 10) to further retract the sheath 104 until at least a portion of the contralateral limb 58 is exposed as shown in FIG. 24.

With the stent-graft 42 at least partially exposed and the proximal suture drum 162 (or proximal suture drum 234 in the embodiment shown in FIGS. 33-38) accessible, the proximal end 144 of the stent 42 may be deployed. As previously described, the user may rotate the proximal suture drum 162, which winds the suture 180 around a proximal portion 198 of the outer surface of the main handle 10 (or in an alternative embodiment, rotation of the proximal suture drum 234 engages the rack 232, which pulls the rack 232 proximally forward within the main handle 10) which in turn, pulls the suture 180 proximally to unwind the suture 180 from the distal suture drum 174. The unwinding of the suture 180 from the distal suture drum 174 causes the distal suture drum 174 to rotate. Rotational motion of the distal suture drum 174 is transferred (by the suture 180) to the inner cannula 22, causing the entire length of the inner cannula 22 to rotate as shown in FIG. 26. Rotation of the inner cannula 22 effects release of the prosthesis retention mechanism 80. For example, as the inner cannula 22 rotates, the proximal apices 66 or suture loops 74 of the stent graft 42 are uncoupled from the coiled member 84 (i.e., in a reverse manner from which the suture loops 74 were initially coupled to the coiled member 84 during assembly and/or manufacture). It should be understood by one skilled in the art that clockwise and/or counterclockwise rotation is merely illustrative and not limiting, and that the handle assembly 8 and its various rotating components can be designed and configured to rotate in either/or a clockwise or counterclockwise direction, or combination thereof.

After release of the top stent 46, and if necessary or desired depending on the particular procedure being performed and the condition of the patient requiring treatment, a second guide wire 256 may be tracked through the contralateral leg 58 and main body 62 of the stent graft 42, to cannulate the contralateral leg 58. A second leg extension stent graft 258 can be fed over the guide wire 256 and into position within the cannulated contralateral leg 58 as shown in FIG. 25. After deployment of the leg extension graft 258 on the contralateral side 58, the second handle 12 may again be moved back in a distal direction relative to the main handle 10 by the user as shown in FIG. 29 to further retract the sheath 104 while simultaneously withdrawing one or more distal trigger wires 208 to thereby deploy the ipsilateral limb 60 of the stent graft 42 as shown in FIG. 27.

To accomplish this, the user may continue rotation of the second handle 12 or, alternatively, the user may employ the "quick release" procedure, which permits longitudinal movement of the second handle 12 relative to the main handle 10, without having to rotate the second handle 12, to thereby retract the sheath 104 and remove the distal trigger wires 208. Whether by continued rotation of the second handle 12 relative to the main handle 10 or implementation of the "quick release" procedure (allowing straight pull-back of the second handle without rotation), the user moves the second handle 12 distally along the main handle 10 for a travel distance indicated by reference number 212 in FIG. 28. In one non-limiting example, this travel distance 212 may be the distance of longitudinal movement of the second handle 12 necessary to facilitate distal retraction of the sheath 104 a sufficient distance to completely un-sheath the ipsilateral limb 60 of the stent graft 42. By this same action, the distal trigger wire or wires 208 are also withdrawn from the distal end 48 of the prosthesis 42 to complete the stent graft deployment. In the event of a mechanical malfunction of one or more components of the handle assembly 8 described above, the handle end cap 14 can be removed, and the interior 124 of the main handle 10, including the distal suture drum 174 can be accessed and rotated manually.

Once the stent graft 42 has been fully released from the delivery device 2, it is desirable to withdraw the delivery device 2 from the patient's body. If the quick release procedure described above has already been employed, then the nut 142 has already been disengaged or disassociated from the main handle 10, allowing the second handle 12 to slide freely longitudinally along the main handle 10. Thus, the user can slide the second handle 12 in a proximal direction (away from the user) on the main handle 10, thus sliding the sheath connector 108 and sheath 104 proximally and allowing the proximal end of the sheath 104 to extend over all of, part of, or at least distal portion 82 of the nose cone 18 of the device 2 so as to "hub" or "recapture" a portion of the nose cone within the sheath 104. Alternatively, rather than pushing the second handle 12 proximately to re-sheath the nose cone 18, the main handle may be pulled distally relative to the second handle 12, thus pulling the distal portion 82 of the nose cone 18 into the proximal end of the sheath 104. With at least a distal end of the nose cone 18 recaptured within the sheath 104, the delivery device 2 can be withdrawn from the patient's body.

If, however, the user did not employ the quick release procedure to further retract the sheath 104 to expose the ipsilateral limb 60 and/or for distal trigger wire release (but instead the user decided to continue rotating the second handle 12 to move it distally relative to the main handle 10 to accomplish these deployment steps), then, at this time, the second handle 12 is at a distal most position on the main handle (see FIG. 29) but the inner surface of the nut 142 is still threadedly engaged with the outer surface 122 of the main handle 10. Thus, in order to move the second handle 12 proximally for tip re-sheathing or recapture, the user must first move the ring 220 distally on the second handle 12 to move the sleeve 222 distally, allowing the proximal end 150 of the nut to flare or expand radially outwardly and disengage from the threads 132 on the main handle 10. This permits the second handle 12 to now slide freely longitudinally on the main handle 10 and the user may then be able to move the second handle 12 proximally to recapture (re-sheath) the proximal tip as previously described, and then remove the delivery device 2 from the patient to complete the procedure.

The invention claimed is:

1. A handle assembly for a prosthesis delivery device having a proximal end and distal end, the handle assembly comprising:
 a main handle having a proximal end and a distal end;

a prosthesis release actuation mechanism disposed at least partially on the main handle and moveable relative to the main handle;

a motion translating mechanism disposed distal to and operatively connected to the prosthesis release actuation mechanism;

a prosthesis retention mechanism disposed at the proximal end of the delivery device and proximal to a prosthesis retention region and operatively connected to the motion translating mechanism, the prosthesis retention mechanism having a prosthesis capture condition and a prosthesis release condition;

wherein movement of the prosthesis release actuation mechanism causes movement of the motion translating mechanism thereby moving the prosthesis retention mechanism from the prosthesis capture condition to the prosthesis release condition;

wherein the prosthesis release actuation mechanism is circumferentially disposed about the main handle and rotationally moveable relative to the main handle;

wherein rotation of the prosthesis release actuation mechanism in a first direction effects rotation of the motion translating mechanism in a second direction and wherein rotation of the motion translating mechanism effects rotation of the prosthesis retention mechanism in a third direction;

wherein at least one of the first, second and third rotation directions is a different direction.

2. The handle assembly for a prosthesis delivery device of claim 1 further comprising a second handle disposed at least partially on the main handle and at least one of circumferentially and longitudinally moveable relative to the main handle, the second handle having a first position on the main handle in which movement of the prosthesis release actuation mechanism is prevented and a second position on the main handle in which movement of the prosthesis release actuation mechanism is permitted.

3. The handle assembly for a prosthesis delivery device of claim 2, further comprising a sheath operatively connected to the second handle, the sheath extending proximally of the main handle, wherein the at least one of circumferential and longitudinal movement of the second handle retracts the sheath in a distal direction.

4. The handle assembly for a prosthesis delivery device of claim 2, wherein the second handle is threadedly engaged with the main handle.

5. The handle assembly for a prosthesis delivery device of claim 1, wherein the motion translating mechanism comprises a rotatable drum.

6. The handle assembly for a prosthesis delivery device of claim 1, wherein an elongated filamentous material extends between the prosthesis release actuation mechanism and the motion translating mechanism.

7. The handle assembly for a prosthesis delivery device of claim 6 wherein the elongated filamentous material comprises at least one of a suture, string, wire, cord and thread.

8. The handle assembly for a prosthesis delivery device of claim 6 wherein a portion of the elongated filamentous material is wound about the motion translating mechanism.

9. The handle assembly for a prosthesis delivery device as in claim 1 wherein the prosthesis release actuation mechanism is threadedly engaged with an elongated rack mechanism, and wherein rotation of the prosthesis release actuation mechanism moves the rack mechanism longitudinally relative to the main handle.

10. A handle assembly for a prosthesis delivery device of claim 9 wherein an elongated filamentous material extends between a distal end of the rack mechanism and the motion translating mechanism and wherein the filamentous material operatively connects the prosthesis release actuation mechanism to the motion translating mechanism.

11. The handle assembly for a prosthesis delivery device of claim 1, further comprising a cannula extending from the motion translating mechanism to the prosthesis retention mechanism.

12. The handle assembly for a prosthesis delivery device of claim 1 wherein at least one of the first, second and third rotation directions is the same direction.

13. A prosthesis delivery device having a proximal end and distal end, the prosthesis delivery device comprising:

a handle assembly at a distal end of the delivery device, the handle assembly comprising:

a main handle having a proximal end and a distal end;

a prosthesis release actuation mechanism disposed at least partially on the main handle and moveable relative to the main handle;

a motion translating mechanism disposed distal to and operatively connected to the prosthesis release actuation mechanism;

a prosthesis retention mechanism disposed at the proximal end of the delivery device and proximal to a prosthesis retention region and operatively connected to the motion translating mechanism, the prosthesis retention mechanism having a prosthesis capture condition and a prosthesis release condition;

wherein movement of the prosthesis release actuation mechanism causes movement of the motion translating mechanism thereby moving the prosthesis retention mechanism from the prosthesis capture condition to the prosthesis release condition;

wherein the prosthesis release actuation mechanism is circumferentially disposed about the main handle and rotationally moveable relative to the main handle;

wherein rotation of the prosthesis release actuation mechanism in a first direction effects rotation of the motion translating mechanism in a second direction and wherein rotation of the motion translating mechanism in a second direction effects rotation of the prosthesis retention mechanism in the second direction.

14. The prosthesis delivery device of claim 13 further comprising a second handle disposed at least partially on the main handle and at least one of circumferentially and longitudinally moveable relative to the main handle.

15. The prosthesis delivery device of claim 14, further comprising a sheath operatively connected to the second handle and extending proximally of the main handle, wherein the at least one of circumferential and longitudinal movement of the second handle retracts the sheath in a distal direction.

16. The prosthesis delivery device of claim 14, wherein the second handle is threadedly engaged with the main handle.

17. The prosthesis delivery device of claim 13, wherein the motion translating mechanism comprises a rotatable drum.

18. The prosthesis delivery device of claim 13 wherein the prosthesis release actuation mechanism is threadedly engaged with an elongated rack mechanism, and wherein rotation of the prosthesis release actuation mechanism moves the rack longitudinally relative to the main handle.

19. The prosthesis delivery device of claim 18 wherein an elongated filamentous material extends between a distal end of the rack mechanism and the motion translating mechanism and wherein the filamentous material operatively connects the prosthesis release actuation mechanism to the motion translating mechanism.

20. The prosthesis delivery device of claim 13, further including a cannula connected to and extending from the motion translating mechanism to the prosthesis retention mechanism.

\* \* \* \* \*